(12) United States Patent
Vogt et al.

(10) Patent No.: US 10,588,755 B2
(45) Date of Patent: Mar. 17, 2020

(54) KIT FOR BUILDING A CAGE FOR SPONDYLODESIS AND METHOD THEREFOR

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 743 days.

(21) Appl. No.: 15/190,942

(22) Filed: Jun. 23, 2016

(65) Prior Publication Data
US 2016/0374829 A1    Dec. 29, 2016

(30) Foreign Application Priority Data

Jun. 25, 2015  (DE) .................. 10 2015 110 202
Jun. 9, 2016   (CA) ...................................... 2932795

(51) Int. Cl.
*A61F 2/44*     (2006.01)
*A61F 2/30*     (2006.01)
*A44B 18/00*    (2006.01)

(52) U.S. Cl.
CPC ........ *A61F 2/4465* (2013.01); *A44B 18/0065* (2013.01); *A61F 2/3094* (2013.01);
(Continued)

(58) Field of Classification Search
CPC ............ A61F 2/4465; A61F 2002/4475; A61F 2002/448; A61F 2002/4485;
(Continued)

(56) References Cited

U.S. PATENT DOCUMENTS 2,717,437 A    9/1955  Mestral
3,266,113 A *  8/1966  Flanagan, Jr. ..... A44B 18/0053
                                                  24/452
(Continued)

FOREIGN PATENT DOCUMENTS

CA    2845613 A1    9/2014
CA    2846793 A1    9/2014
(Continued)

OTHER PUBLICATIONS

Chinese Office Action from corresponding application dated Jul. 17, 2017.
(Continued)

*Primary Examiner* — Anu Ramana
(74) *Attorney, Agent, or Firm* — Norris McLaughlin, P.A.

(57) ABSTRACT

A modular kit and/or method buildings a cage for spondylodesis, wherein the kit and/or method comprises at least two plates, wherein the plates comprise a biocompatible material and each comprise a planar structure and a plurality of pins projecting from the planar structure of the plates, wherein the pins each comprise at least one latching element, wherein the pins are elastically deformable and are arranged sufficiently close to each other on the planar structure such that pressing planar structures studded with pins of several plates onto each other causes the latching elements of different plates to snap into each other, wherein at least two of the at least two plates comprise a recess with a diameter of at least 5 mm.

25 Claims, 22 Drawing Sheets

Figure 1:
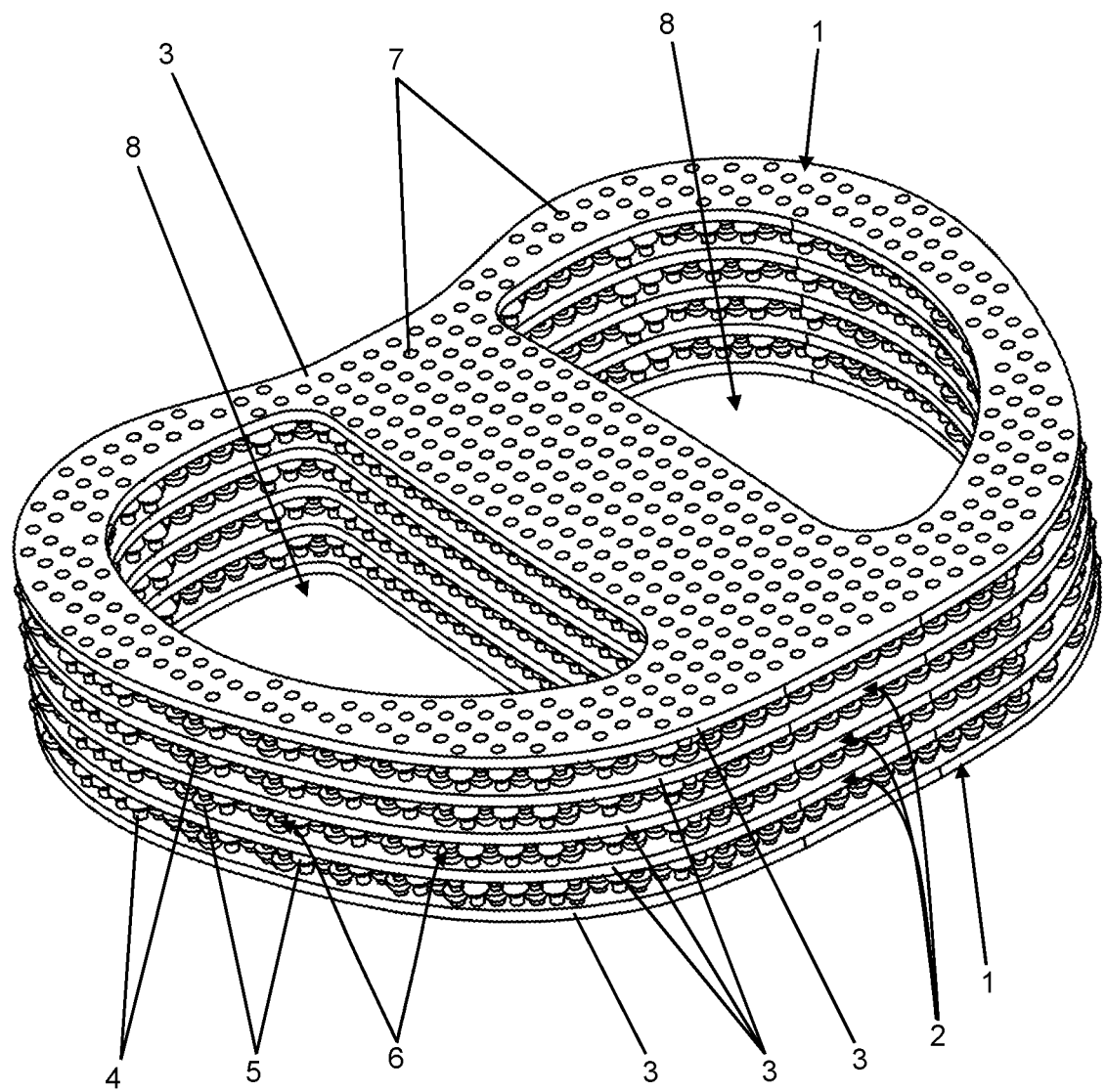

(52) U.S. Cl.
CPC ...... *A61F 2/4455* (2013.01); *A61F 2002/305* (2013.01); *A61F 2002/30179* (2013.01); *A61F 2002/30299* (2013.01); *A61F 2002/30331* (2013.01); *A61F 2002/30467* (2013.01); *A61F 2002/30556* (2013.01); *A61F 2002/30599* (2013.01); *A61F 2002/30604* (2013.01); *A61F 2002/30622* (2013.01); *A61F 2002/30784* (2013.01); *A61F 2002/30971* (2013.01); *A61F 2002/30973* (2013.01); *A61F 2002/30985* (2013.01); *A61F 2002/4475* (2013.01)

(58) Field of Classification Search
CPC .......... A61F 2220/0025; A61F 2/30734; A61F 2250/006
See application file for complete search history.

(56) References Cited

U.S. PATENT DOCUMENTS

| | | | |
|---|---|---|---|
| 3,408,705 A | 11/1968 | Kayser et al. | |
| 3,808,648 A * | 5/1974 | Billarant | A44B 18/0053 24/442 |
| 4,290,174 A | 9/1981 | Kalleberg | |
| 5,026,373 A | 6/1991 | Ray et al. | |
| 5,077,870 A | 1/1992 | Melbye et al. | |
| 5,192,327 A | 3/1993 | Brantigan | |
| 6,159,211 A | 12/2000 | Boriani et al. | |
| 8,906,095 B2 | 12/2014 | Christensen et al. | |
| 9,034,356 B2 * | 5/2015 | Shimp | A61L 27/446 424/423 |
| 9,737,414 B2 | 8/2017 | Felt et al. | |
| 2004/0249471 A1 | 12/2004 | Bindseil et al. | |
| 2006/0015184 A1 | 1/2006 | Winterbottom et al. | |
| 2006/0195191 A1 | 8/2006 | Sweeney, II et al. | |
| 2007/0100452 A1 | 5/2007 | Prosser | |
| 2007/0162132 A1 * | 7/2007 | Messerli | A61B 17/68 623/17.11 |
| 2008/0119853 A1 | 5/2008 | Felt et al. | |
| 2010/0286778 A1 | 11/2010 | Eisermann et al. | |
| 2014/0133279 A1 | 5/2014 | Khuri-Yakub et al. | |
| 2014/0207238 A1 | 7/2014 | Theofilis et al. | |
| 2014/0207245 A1 | 7/2014 | McMinn | |
| 2014/0336652 A1 | 11/2014 | Christensen et al. | |
| 2014/0358235 A1 | 12/2014 | Fox et al. | |

FOREIGN PATENT DOCUMENTS

| | | |
|---|---|---|
| CH | 295638 A | 1/1954 |
| CN | 1426290 A | 6/2003 |
| CN | 101600404 A | 12/2009 |
| DE | 1610318 A | 1/1966 |
| DE | 1625396 A1 | 6/1970 |
| DE | 102004048464 A1 | 4/2006 |
| DE | 102006015100 A1 | 10/2007 |
| DE | 102006015145 A1 | 10/2007 |
| DE | 102006015148 A1 | 10/2007 |
| EP | 2 832 320 A1 | 2/2015 |
| JP | H 07-79809 A | 3/1995 |
| JP | 2007-519492 A | 7/2007 |
| JP | 2014-518512 A | 7/2014 |
| WO | 01/066044 A | 9/2001 |

OTHER PUBLICATIONS

Cutler, Aaron R., et al., "Comparision of polyetheratherketone cages with femoral cortical bone allograft as a single-piece interbody spacer in transforaminal lumbar interbody fusion", Journal of Neurosurgery, Dec. 2006, pp. 534-539, vol. 5, New York, New York, USA.

Australian Office Action for related Australian Patent Application No. 2016204025 dated Nov. 18, 2016.

* cited by examiner

KIT FOR BUILDING A CAGE FOR SPONDYLODESIS AND METHOD THEREFOR

This application claims priority of German Patent Application No. 10 2015 110 202.1, filed on Jun. 25, 2016, and Canadian Patent Application No. 2,932,795, filed on Jun. 9, 2016, their entire contents of which are incorporated herein by reference.

The invention relates to a modular kit for building a cage for spondylodesis. The invention also relates to a method for producing such a cage as well as a cage for spondylodesis.

Accordingly, the subject of the invention is also a cage for spondylodesis of vertebral bodies with adjustable height and a method for producing cages with adjustable height.

Spondylodesis (vertebral fusion) is used to stiffen two or more vertebral bodies in the cervical, thoracic and lumbar spine. Spondylodesis (vertebral fusion) is used for unstable breakages of vertebral bodies, congenital (inborn) scoliosis and spondylolisthesis. Here, two or more vertebral bodies which lie one on top of the other are joined together with the aid of bolts, plates and rods. Cages are inserted into the intervertebral space, which create a distance between the vertebral bodies which lie one on top of the other, thus avoiding compression of the spinal cord and the nerves which emanate from it. Further, the cages serve to transmit force between the vertebral bodies. The cages usually contain an open axial hollow chamber. This hollow chamber can for example be filled with bone replacement material such as calcium phosphates, or also with autologous cancellous bone (Aaron R Cutler A. R., et. al.: Comparison of polyetheretherketone cages with femoral cortical bone allograft as a single-piece interbody spacer in transforaminal lumbar interbody fusion. J. of Neurosurgery. Spine 5, No. 6 (2006): 534-539.). Bone tissue between the vertebral bodies can grow into this hollow chamber, so that the vertebral bodies are connected via the newly formed bone. For the clinical success of the cages, it is essential that the physiologically correct distance between the vertebral bodies is maintained through the height of the cages used. As a result, a situation wherein the cages are too high or too low must be avoided at all costs. It is therefore standard procedure for manufacturers to offer cages of different heights. As an alternative, cages are also known in which the height of the cage can be individually adjusted. Examples of these are patent applications US 2014/358 235 A1, CA 2 846 793 A1, CA 2 845 613 A1 and US 2014/207 238 A1. These cages are mechanically sophisticated and have a relatively complex structure. Furthermore, due to their complex structure they are relatively costly and not easy to handle.

The object of the invention is thus to overcome the disadvantages of the prior art. In particular, a mechanically stable cage is to be developed the height of which can be adjusted in a highly simple manner without the use of technical aids. The cage to be developed should contain no complex levers and/or bolt systems. Furthermore, the cage should be as porous as possible in order to guarantee a bony consolidation of the cage. Additionally, the cage must be biocompatible. The cage should also form a porous body with a stable form, have open porosity and be mechanically stable. The porosity and the size of the pores should here be sufficient and suitable for the human bone of a patient treated with the cage can grow into the pores of the cage.

The objects according to invention are achieved by a modular kit for building a cage for spondylodesis, the kit comprising at least two plates, wherein the plates consist of a biocompatible material and each comprising a planar structure and a plurality of pins projecting from the planar structure of the plates, wherein the pins each comprise at least one latching element, wherein the pins are deformable elastically and are arranged sufficiently close to each other on the planar structure such that pressing the planar structures studded with pins of several plates onto each other causes the latching elements of different plates to snap into each other, wherein at least two of the at least two plates comprise a recess with a diameter of at least 5 mm.

Preferably, it can be provided that the at least two plates consist of a biocompatible plastic, a biocompatible metal and/or a biocompatible metal alloy. Biocompatible metals and biocompatible metal alloys are preferred according to the invention in order to produce the plates of the kit from them.

Preferably, all of the at least two plates comprise a recess with a diameter of at least 5 mm.

When they snap into each other, the latching elements of the pins of the plates grip into latching elements of pins of adjacent plates in such a manner that the plates can no longer be separated from each other, but also can no longer be moved towards each other by the plates being further pressed together. The latching elements can be formed by hooks, grooves, undercuts, snap-in elements and/or counter snap-in elements.

The term "planar" is used with reference to planar bodies and bodies derived from planar bodies, which are respectively formed by a closed or perforated plate-like base body. Perforated planar structures are here preferred for the plates to be connected to the vertebral bodies, since due to this perforation or due to the pores formed by the perforation, bone tissue can grow into the plates. It is very particularly advantageous and preferred according to the invention when one perforation or one pore is arranged alongside each pin. Then, after several plates have snapped into place, two porous base areas form for connection to the vertebral bodies, which when suitable material such as tantalum is selected are osteoconductive.

When pressure acts on the plates of the kit which are touching each other, according to the invention these form a mechanically stable connection.

With kits according to the invention it can be provided that the plates which are snapped into each other form a cage consisting of plates which are snapped into each other with at least one open axial hollow chamber, wherein the hollow chamber has a diameter of at least 5 mm, wherein preferably the plates which are snapped into each other form a cage consisting of plates which are snapped into each other with two open axial hollow chambers, wherein the two hollow chambers have a diameter of at least 5 mm respectively.

As a result, the interior of the cage is formed by the at least one open axial hollow chamber. The bone can grow through the at least one open axial hollow chamber, so that the two vertebral bodies can grow together.

Further it can be provided that each of the at least two plates comprises a recess with a diameter of at least 5 mm, wherein preferably at least one open axial hollow chamber of the cage produced from the plates can be created with the recesses of the at least two plates.

As a result, due to the fact that the at least two plates lie on top of each other and snap into each other, the recesses can be arranged in relation to each other that they lie one on top of the other, so that the recesses that lie one on top of the other form the at least one open axial hollow chamber into which the bone of the two adjacent vertebral bodies can grow.

With the invention it is also recommended that the wall of the at least one open axial hollow chamber of a cage formed from the at least two plates which are snapped into each other and/or the boundaries of the recesses of the at least two plates are filled with autologous bone material.

As a result, autologous bone growth is supported so that the bone of the patient can more easily and quickly grow through the recesses or the at least one open axial hollow chamber.

With one advancement it is recommended that the plates which are snapped into each other form a porous cage consisting of plates which are snapped into each other, preferably an open-pore cage made of plates which are snapped into each other.

As a result, the bone can grow at least in some areas into the pores of the cage formed by the plates. Furthermore, it is recommended with the invention that the pores of the open-pore cage made of several plates are interconnecting and osteoconductive, wherein preferably the pores have a free profile of between 0.1 mm and 1 mm, particularly preferably between 0.25 mm and 0.9 mm. This ensures that the bone can grow together well with the pores of the cage produced from the kit. The side walls of the cage which project outwards can according to the invention be completed by a closed wall. For this purpose, on the at least two plates, a circumferential edge can be provided which when snapped into an adjacent plate creates a form-fit completion with the edge of the adjacent plate, thus forming the closed wall.

With preferred kits, it can be provided according to the invention that the modular kit for building a cage for spondylodesis has an adjustable height and for this purpose preferably comprises three plates so that different heights can be set through the optional use of one inner plate or of several inner plates.

As a result, a cage with different heights is made possible which is particularly easy to construct from the kit. The kit can thus be variably used for different patient requirements and adapted to the anatomical conditions.

With a further development, it can also be provided that the at least two plates comprise a completing circumferential edge, so that the plates which are snapped into each other form a cage with a wall that is closed to the outside, wherein preferably, the edges are interlocked.

As a result, it is possible to prevent the material exiting outwards from the interior of the cage that has been produced.

Further, it can be provided within the scope of the present invention that at least one group of the at least two plates, preferably at least one group of the at least four plates, are of the same shape with regard to the form of the planar structure or are essentially of the same shape, so that they can be stacked one on top of the other and/or snapped into each other in a form-fit manner in the direction vertical to the planar structures.

As a result, with the kit, a cage can be produced from the kit which is variable in terms of height but which is clearly formed in terms of its circumference.

Here, it can be provided that at least two groups of the at least two plates, preferably at least two groups of the at least four plates, are of the same shape with regard to the form of the planar structure or are essentially of the same shape, so that they can be stacked one on top of the other and/or snapped into each other in a form-fit manner in the direction vertical to the planar structures, wherein the at least two groups comprise different geometries as regards the planes of the planar structures.

As a result, with the kit, a plurality of different cages can be constructed for different anatomical conditions.

Further, it can be provided that at least two outer plates of the at least two plates which are provided for direct connection with the vertebral bodies are osteoconductive due to pores in the planar structures and/or the planar structures comprise an attachment surface without pins, which is designed to be placed against the vertebral bodies, wherein preferably the attachment surface comprises peaks or naps for connecting the plates to the bone of the vertebral bodies.

The peaks or naps can be pressed into the bones of the vertebral bodies. Alternatively or in addition, eyelets or bore holes can be provided in the planar structure of the at least two outer plates, through which the at least two outer plates can be bolted or otherwise connected (e.g. with nails) to a vertebral body. Even when both sides of the at least two plates comprise pins, sharp tips can be provided for attachment to the bone surface, for which purpose the pins should protrude with the latching elements. With embodiments with sharp tips, a plate can be anchored by driving the sharp tips into the bone tissue of the vertebral body. Building on this, further plates from the kit can then be applied and snapped in.

Outer plates of this type can be used for direct planar attachment on the bone. With the eyelets or bore holes, it is possible to bolt the plate onto the bone tissue and to apply as many further plates from the kit as required and then to snap them in. As a result, three-dimensional cages with variable heights can be constructed in a load-bearing manner.

According to the invention, the pores are preferably rounded off, in particular they do not comprise any sharp-edged contours. In a particularly preferred manner, the pores in the planar structure of the plate have a free profile of between 0.25 mm and 1 mm, particularly preferred between 0.3 mm and 0.9 mm.

Due to the pores, the cage produced from the plates of the kit can be attached to the adjacent vertebral bodies in a particularly stable manner.

According to a preferred embodiment of the kit according to the invention, it can be provided that at least three plates are provided, with at least one inner plate and at least one outer plate, wherein one inner plate and in addition at least one outer plate respectively always form a planar group, wherein each outer plate comprises a recess so that this outer plate encloses in a form-fit manner the inner plate of the same planar group or a different outer plate of the same planar group on the plane of the planar structures.

As a result, cages with different cross sections can be produced using the kit.

Furthermore, it can be provided that the planar structure of at least one of the plates, in particular of at least one inner plate, has a gradient in the thickness, wherein preferably, the area with the greatest thickness is maximum 100% thicker than the area with the least thickness.

Due to a kit of this type, curved or inclined cages can also be produced, with which the positions of the vertebral bodies can be adapted to each other, or taken into account.

Further, it is recommended that on one planar structure of at least one plate, preferably on the planar structures of the outer plates, at least two positioning aids, in particular positioning pins, are provided, wherein with the positioning aids the orientation of the plates to be joined together in relation to each other is specified.

This ensures that the plates can only be joined together in the desired orientation. As a result, the degree of possibility of misuse is reduced.

Preferably, it can be provided that the latching elements are mushrooms, hooks, undercuts, snap-in elements and/or counter snap-in elements.

These latching elements are particularly well suited for a mutual snapped-in connection. Textile connections such as hook and loop connections with easily deformable fibres are by contrast unsuitable according to the invention since with these, no dimensionally stable, pressure-resistant cages can be constructed for spondylodesis.

With one advancement it is recommended that the distance between the latching elements and the planar structure of the at least two plates is between 0.3 mm and 2 mm, preferably between 0.5 mm and 1 mm.

As a result, a sufficiently stable snapped-in connection is achieved between the latching elements, and at the same time sufficient bending of the pins is made possible in order to connect the latching elements.

According to an advancement of the invention it can be provided that at least one of the at least one latching elements per pin has a truncated cone shape, wherein the longitudinal axes of the pins form the longitudinal axes of the cones and wherein the sheath of the cones points towards the outer side that faces away from the planar structure of the at least one plate.

As a result, the at least two plates can be connected in particularly stable manner by means of the latching elements shaped as truncated cones. Moreover, said shaping prevents surrounding soft tissue and bone tissue from being injured following implantation of the cage.

Moreover, the invention can provide at least one of the at least one latching elements per pin is designed in the form of a hook and/or as a mushroom head.

The hooks and/or the mushroom heads provide for stable and non-detachable connection of the plates to each other. If the latching elements are mushroom head-shaped, they can possess, for example, a collar at the mushroom head edge provided in the direction of the planar structure such that hook-shaped latching elements of other plates can engage this thus generated undercut, whereby an irreversible, non-detachable interlocked or snapped-in connection between the plates is produced. It is also feasible, and preferred according to the invention, that at least one plate contains various latching elements or various pins with different latching elements. Accordingly, a plate can simultaneously possess hooks and mushroom heads as latching elements, both on the same pin and on different pins.

In a preferred embodiment, the latching elements are provided as mushroom heads. In a particularly preferred embodiment, the mushroom heads are shaped appropriately such that the mushroom heads comprise a conical undercut on the side facing the surface of the respective planar structure. As a result, hook-shaped snap-in elements can be interlocked irreversibly and non-detachably with said mushroom heads. If the shapes of the undercuts and of the mushroom heads match properly, further propulsion of the mushroom heads can be prevented so that the mushroom heads snap into the undercuts.

According to a preferred advancement, it can be provided that the pins between the planar structure of the at least two plates and at least one of the at least one latching elements contain a circumferential groove as a counter-latching means, into which latching elements of other plates can snap, preferably snapping into place in such a manner that no further movement of the latching elements along the pins is possible.

This also enables a particularly stable connection between the plates.

Particularly advantageous kits can provide that the at least one plate is made from biocompatible plastic, stainless steel, titanium, a titanium alloy, tantalum, a tantalum alloy or composites of said materials.

Said materials are particularly well-suited for medical purposes and can be used to attain the suitable elastic properties of the pins. It is preferred, according to the invention, to produce plates consisting of metal or metal alloys by selective laser sintering or by melting with electron beams, preferably by a 3D printing method.

The biocompatible plastic material can be biodegradable. Polylactides, polyglycolides, polycaprolactones and polyester formed from different a-hydroxy carboxylic acids can be used for this purpose. Conceivable non-biodegradable plastic materials include polyamides, polyimides, polyetherketone, and polysulfone. Plates made of these non-biodegradable and biodegradable plastic materials can be produced by selective laser sintering.

According to a preferred embodiment of the present invention, it is recommended that adjacent pins which are arranged on the same side of a first plate of the at least two plates are of such a distance from each other that following an elastic deformation due to a snapped-in connection with a latching element of one second plate of the at least two plates, the pins of the first plate enable at least two snapped-in connections with at least two further latching elements of the second plate, and preferably enable at least three snapped-in connections with three further latching elements of the second plate.

Due to multiple snapped-in connections of the plates, a particularly stable cage can be formed from the plates in the kit.

It can also be provided that the at least two plates are filled with inorganic or organic particular bone replacement material and/or autologous or also allogenic cancellous bone.

In this manner, healing of the bone and the connection between the cage and the bone of the vertebral bodies can be accelerated.

Further, the invention can provide that the at least two plates are coated with one or more pharmaceutical agents from the groups of antibiotics, bisphosphonates, steroids, non-steroidal anti-inflammatory drugs, growth factors, and cytostatic agents.

As a result, the cage has a pharmacological effect that contributes to the healing of the patient treated with the cage. Preferred agents from the group of antibiotics are, in particular, gentamicin, tobramycin, amikacin, vancomycin, teicoplanin, clindamycin, and daptomycin.

Further it can be provided that the pins are arranged in rows of three or more pins respectively and that between said three or more rows a strip of unoccupied surface of the planar structure remains, or that a grouped or nest-shaped arrangement of pins with latching elements is provided.

As a result, space is provided for the deformation of the pins with the latching elements for the snapped-in connection.

Further it can be provided that the pins of the at least two plates extend vertically or at an angle of between 60° and 90°, preferably at an angle of between 80° and 90°, from the planar structures of the at least two plates.

As a result, it is achieved that the plates can later be particularly easily connected to each other. Moreover, this achieves an even load-bearing capacity of the cage.

According to a preferred embodiment of the present invention, it can be provided that the kit comprises at least two outer plates for connection with the vertebral bodies and at least one inner plate for setting the height of the cage to be built, wherein each of the at least one inner plate comprises pins with latching elements on both sides of the planar structure, and preferably the at least two outer plates comprise pins with latching elements only on one side of the planar structure.

As a result, the height of the cage to be built can be set in a particularly simple manner by omitting or adding inner plates.

It is also recommended that the latching elements are provided on the sheath surface of the pins.

Thus a stable connection can be achieved between the pins and thus between the plates.

Preferred kits according to the invention can provide that plates pressed into each other irreversibly interlock and/or snap into each other.

As a result, it is ensured that the plates of the fully formed cage do not detach from the cage.

With an advancement of the present invention, it is recommended that the at least two plates without the projecting pins or the planar structure of the plates have a thickness of maximum 2 mm, preferably a thickness of between 0.25 mm and 1.5 mm, and in a particularly preferred manner, a thickness of between 0.5 mm and 1.5 mm.

The thickness of the at least two plates or of the planar structure can also be described as the thickness of the plates or planar structure, and is the dimension of the plate without the pins, which is arranged vertical to the planar structure of the plate. As a result, it is achieved that the plates can either be sufficiently strongly bent or deformed in order to be adjusted to the treatment situation, or that different construction heights of the cage can be achieved with just a few plates through the use of plates of differing thickness.

Furthermore, it can be provided that the at least two plates are produced using a generative 3D printing method.

This enables the plates and thus the cage to be produced at a low cost.

It can also be provided that two latching elements are arranged in sequence on the sheath surface of the pins, and in a particularly preferred manner, three latching elements are arranged in sequence on the sheath surface of the pins.

By this means, it is possible to snap in plates at different distances from each other. As a result, greater flexibility is achieved when forming the cage. However, here it is difficult to achieve the necessary stability of the cage vertical to the plane of the planar structure.

It can also be provided that the at least one plate is designed in the form of a surface with rounded corners, preferably in a kidney shape.

Through this forming, the plates and the cages produced from them are particularly well adjusted to the vertebral bodies to be treated.

Further, it can be provided that continuous pores are contained in the planar structure of the at least two plates, wherein the depth of the pores vertical to the planar structure of the at least two plates is at least 0.25 mm, preferably at least 0.4 mm.

As a result, it can be ensured that the pores are stably enclosed by the bone and with a uniform shape. The plates thus recreate cancellous tissue that corresponds to a normal bone structure, and can grow together well with said bone structure and thus with the vertebral bodies.

It can also be provided that the at least one plate is plastically or elastically deformable in the planar structure.

As a result, the at least one plate can be particularly easy adapted to different treatment situations.

The objectives that form the basis of the present invention are also attained by means of a method for producing a cage for spondylodesis with a kit of the type according to the invention, in which several plates are pressed against each other, wherein the plates snap into each other and form the cage.

With this method, it can also be provided that the pins with the latching elements of the at least two plates are brought into contact with each other and that subsequently, by pressing the plates against each other, the pins with the latching elements snap into each other.

When pressure acts on the plates of the kit that are touching each other, according to the invention, said plates then form a mechanically stable connection.

With one advancement, it is recommended that no, one or several inner plates are inserted between two outer plates depending on the thickness desired of the cage to be produced, wherein the plates are snapped into each other by being pressed on top of each other and as a result are firmly connected to each other.

The objectives that form the basis of the invention are further attained by means of a cage for spondylodesis constructed of at least two plates from a kit according to the invention and/or produced using a method according to the invention.

Finally, the objectives that form the basis of the present invention were also attained through the use of such a cage for spondylodesis in accident surgery, orthopaedics or veterinary medicine.

The invention is based on the surprising finding that plates that mechanically snap into each other can be used as components of a kit for producing a cage for spondylodesis. Here, the plates can be arranged in layers, wherein the cage thus formed is rigid and non-compressible after the desired three-dimensional structure has been formed without chemical hardening reactions, such as radical polymerisations or a complex mechanism for stable setting of the height being necessary. The plates are preferably flexible in a limited scope and can thus be brought into the correct form, and snap into each other through pressure and in so doing are connected to each other. When the formed plates snap into each other, the plates stabilise among each other, so that the three-dimensional cage that is created is rigid and dimensionally stable. When the plates are connected to each other by being pressed on top of each other from different directions and with sufficient force, it can be ensured that a sufficient number of interlocking connections and snap-in connections ensue that the cage produced is dimensionally stable and able to withstand mechanical loads. Due to a suitable form and size of the plates, a cage is thus formed which is sufficiently mechanically stable for medical use and that can be appropriately designed for the form of treatment situation. The bone can preferably grow into pores provided in the cage that is connected through pressure and thus form a permanent connection with the cage. Through at least one open axial hollow chamber in the cage, the bone can grow together originating from the vertebral bodies and rigidify the joint of the vertebral bodies.

Surprisingly, it was found that the plates of the kit according to the invention can be attached to the vertebral bodies in layers and through simple manual compression or with the aid of a tappet be hardened to form a homogeneous body with the individual layers (or plates) forming a snapped-in connection. A hardening of the cage according to the invention is enabled through simple compression of plates that lie in contact with each other over the surfaces. A load-bearing connection of two vertebral bodies is possible with the planar material according to the invention (i.e. the plates of the kit according to the invention).

Mechanically interlocking systems following the design principles of hook and loop fasteners have been known for several decades. The principle of the hook and loop fastener was first described by de Mestral in CH 295 638 A. Said principle has been developed further and is put to use in a wide range of reversibly closing hook and loop closures. Exemplary refinements are described in the publications DE 1 610 318 A1, DE 1 625 396 A1, U.S. Pat. Nos. 5,077,870 A, and 4,290,174 A.

An interesting refinement followed later, in which reversibly hook-and-loop-closing steel belt systems for high mechanical load applications and applications at high temperatures were developed (DE 10 2004 048 464 A1, DE 10 2006 015 100 A1, DE 10 2006 015 145 A1, DE 10 2006 015 148 A1).

Within the scope of the present invention, it was surprisingly found that such systems or such functional principles can be used for the construction of cages for spondylodesis, or are transferable to plates for the production of cages for spondylodesis. Here, it can be advantageous for the cages that connections of such a type do not close tightly, but that intermediate chambers remain as an open-pore structure. The interconnecting pores that are formed in the cage as a result can grow together with the bone and thus generate a stable connection between the bone and the cage. For this purpose, it must be ensured that the pores in the plates have a sufficiently free profile. The pores are described as osteoconductive when the bone can grow into the pores and thus connect with the cage formed from the plates.

The invention is thus based on the idea that a cage consisting of at least one distal and one proximal plate can be compiled, wherein between the plates, depending on the desired height of the cage, one or more intermediate plates can be inserted. The connection between the plates is achieved through "burdock type" snap-in connections of latching elements, which are arranged on the surface of the plates. The plates can be connected to each other by the medical user simply by pressing them together axially.

An exemplary embodiment of the present invention, and one which is particularly preferred according to the invention, is a cage with adjustable height which is compiled of at least two plates, in which on at least one side, three or more elastically deformable pins are arranged which on one pin end have at least one latching element respectively, and wherein the at least three or more pins respectively of the distal plate, the proximal plate and the intermediate plates are positioned so closely to each other that when there is contact with the pins of the plates that each lie in contact with each other, said pins interlock under the effect of the pressure and form a cage that is pressure-resistant in the axial direction.

The structure of the plates is designed in such a manner that when the plates are pressed together, plates that come into contact with each other irreversibly snap into each other and form a cage consisting of plates that have snapped into each other.

A cage according to the invention consists for example of a) A distal (outer) plate on the proximal side of which three or more elastically deformable pins are arranged, which on one pin end respectively have at least one latching element b) A proximal (outer) plate, on the proximal side of which three or more elastically deformable pins are arranged, which on one pin end respectively have at least one latching element c) One or more intermediate plates (inner plates), on the distal and proximal side of which three or more elastically deformable pins are arranged respectively, which on one pin end respectively have at least one latching element, and d) Wherein the three or more pins respectively of the distal plate, the proximal plate and the intermediate plates are positioned so closely to each other that when the pins come into contact with the plates which each lie in contact with the other, said pins interlock under the effect of the pressure and form a cage that is pressure-resistant in the axial direction.

It is very particularly advantageous when alongside each pin with a latching element a perforation is arranged in the plates, which causes an open porous body to be formed following the snap-in connection of several plates, which when suitable material is selected, such as tantalum, is osteoconductive.

According to the invention it can be provided that the at least two plates, in particular the proximal plate, the distal plate and the intermediate plates, are formed in a ring shape or an elliptical ring shape, or in the shape of two rings that lie in contact with each other. This means that in the at least one axial hollow chamber of the cages, common bone replacement materials such as tricalcium phosphate, or also autologous bone material, can be used. As a result, a bony through-structure of the cage is facilitated.

It is advantageous when the at least two plates, in particular the proximal plate, the distal plate and the intermediate plates, contain perforations that have a diameter in the range of 300 μm to 3000 μm. These perforations permit bone tissue to grow in.

According to the invention, an exemplary method is furthermore provided for producing a cage for spondylodesis. This method is characterised by the fact that between two outer plates (the distal plate and the proximal plate), depending on the desired height of the cage, one or more intermediate plates are arranged, and the plates are pressed against each other so that the latching elements of the plates interlock and a connection between the plates is formed through the form-fit connection of the latching elements. With the method, the plates are advantageously laid one on top of the other in such a manner that the outer edges of the plates are arranged flush over each other.

Figure 2:
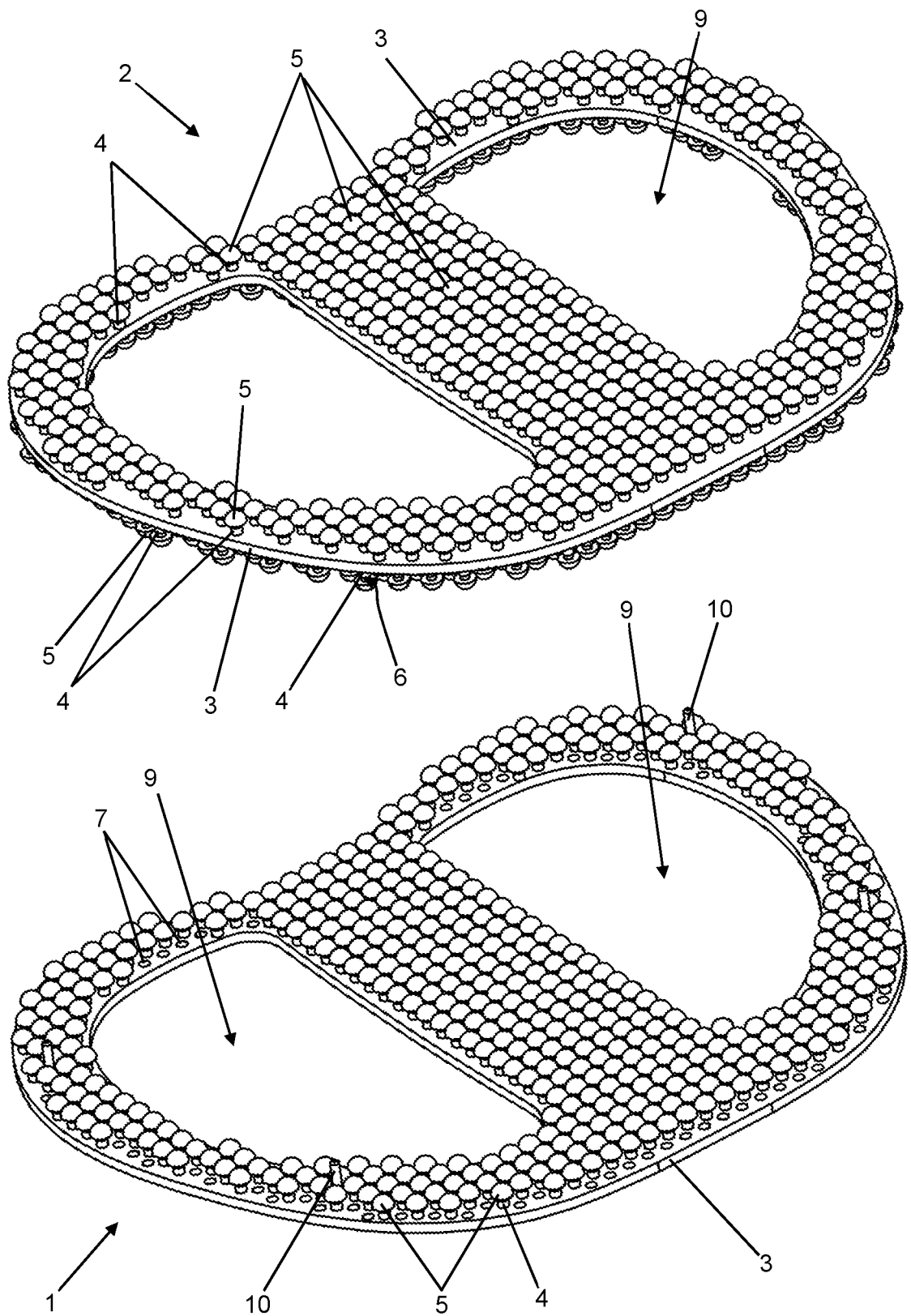
Figure 3:
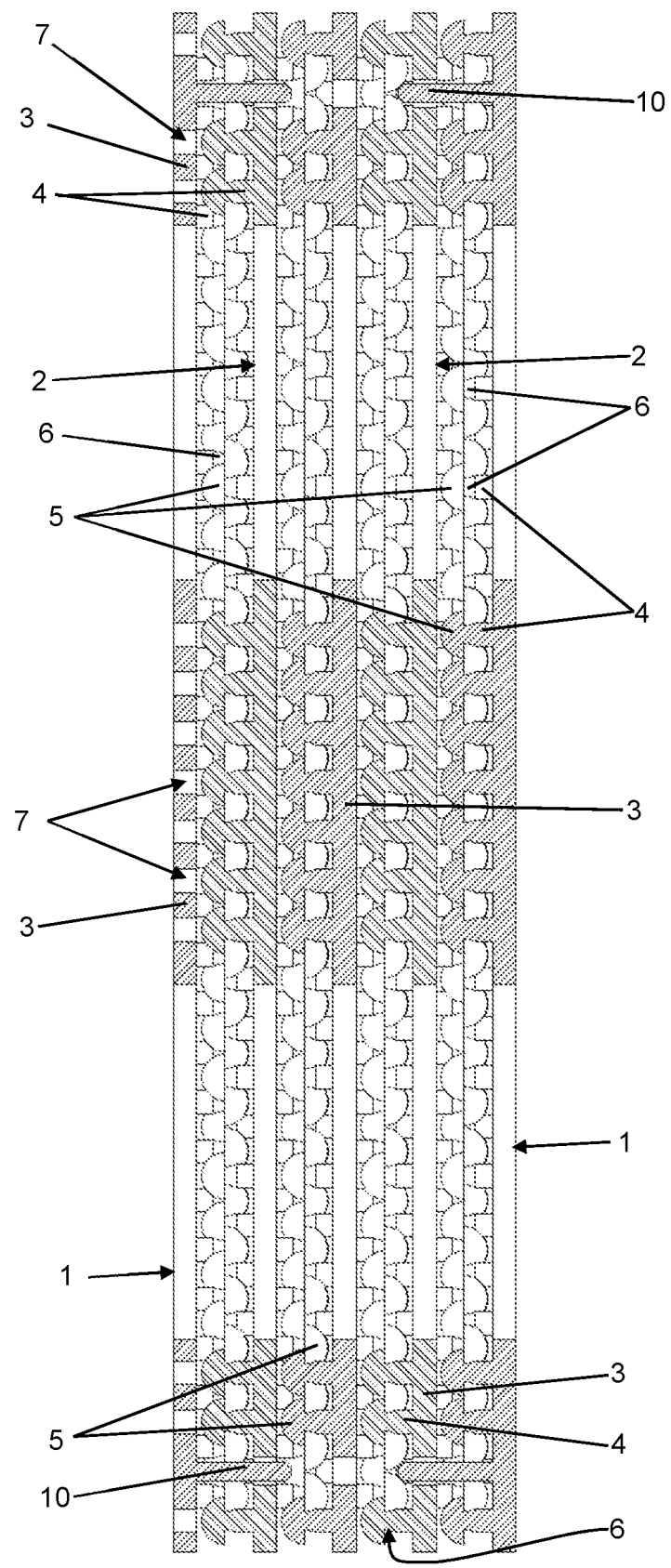

Below, further exemplary embodiments of the invention will be explained with reference to twenty-two schematic figures, although without thereby restricting the invention. In which:

FIG. 1: shows a schematic perspective view onto a cage according to the invention which is constructed of five plates from a kit according to the invention FIG. 2: shows a schematic perspective view onto two of the plates according to FIG. 1, which are not snapped into each other FIG. 3: shows a schematic cross-sectional view through the five snapped-in plates of the cage according to FIG. 1

Figure 4:
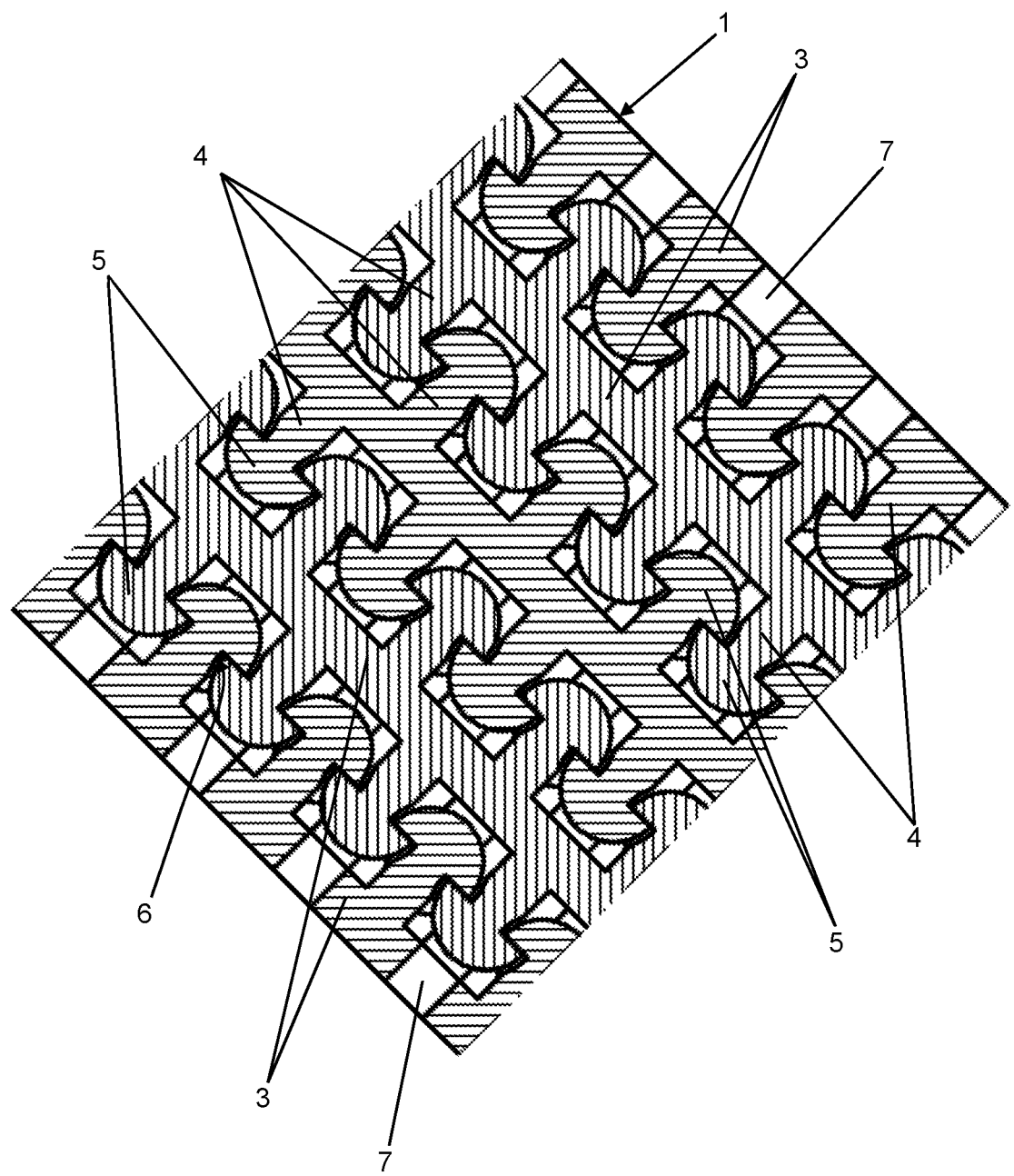

FIG. 4: shows an enlarged representation of a schematic cross-sectional view through the five snapped-in plates of the cage according to FIG. 1

Figure 5:
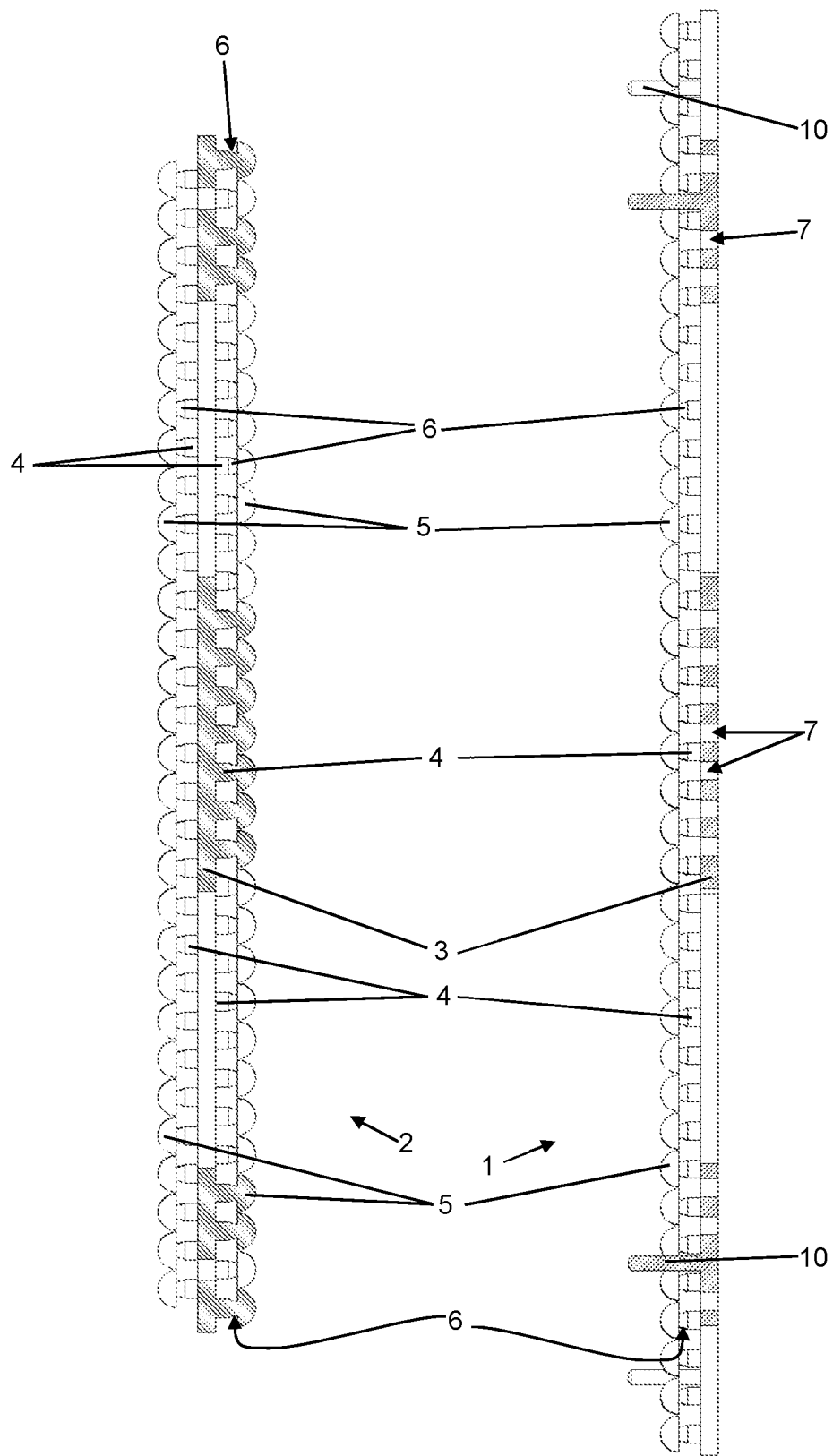
Figure 6:
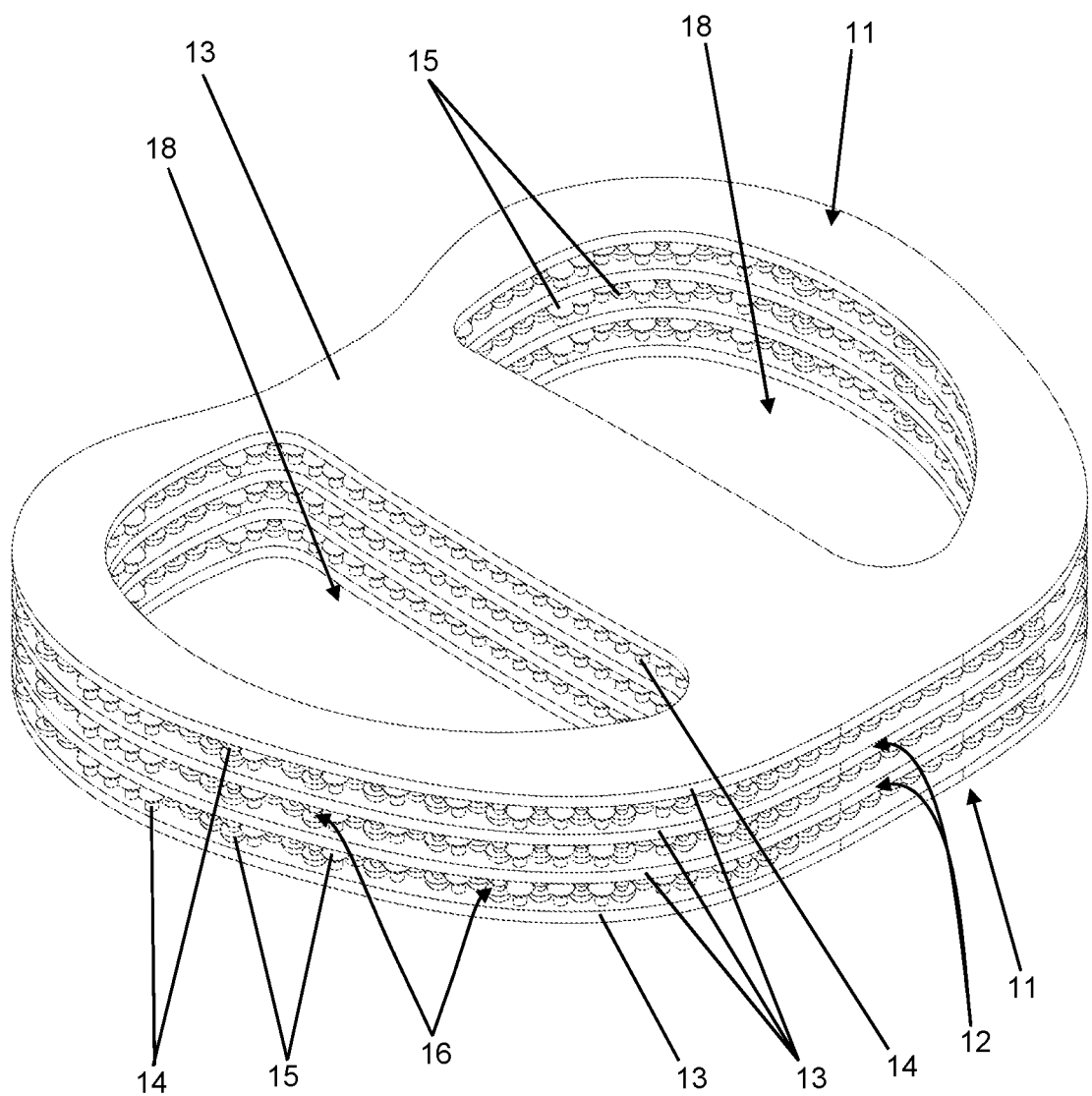
Figure 7:
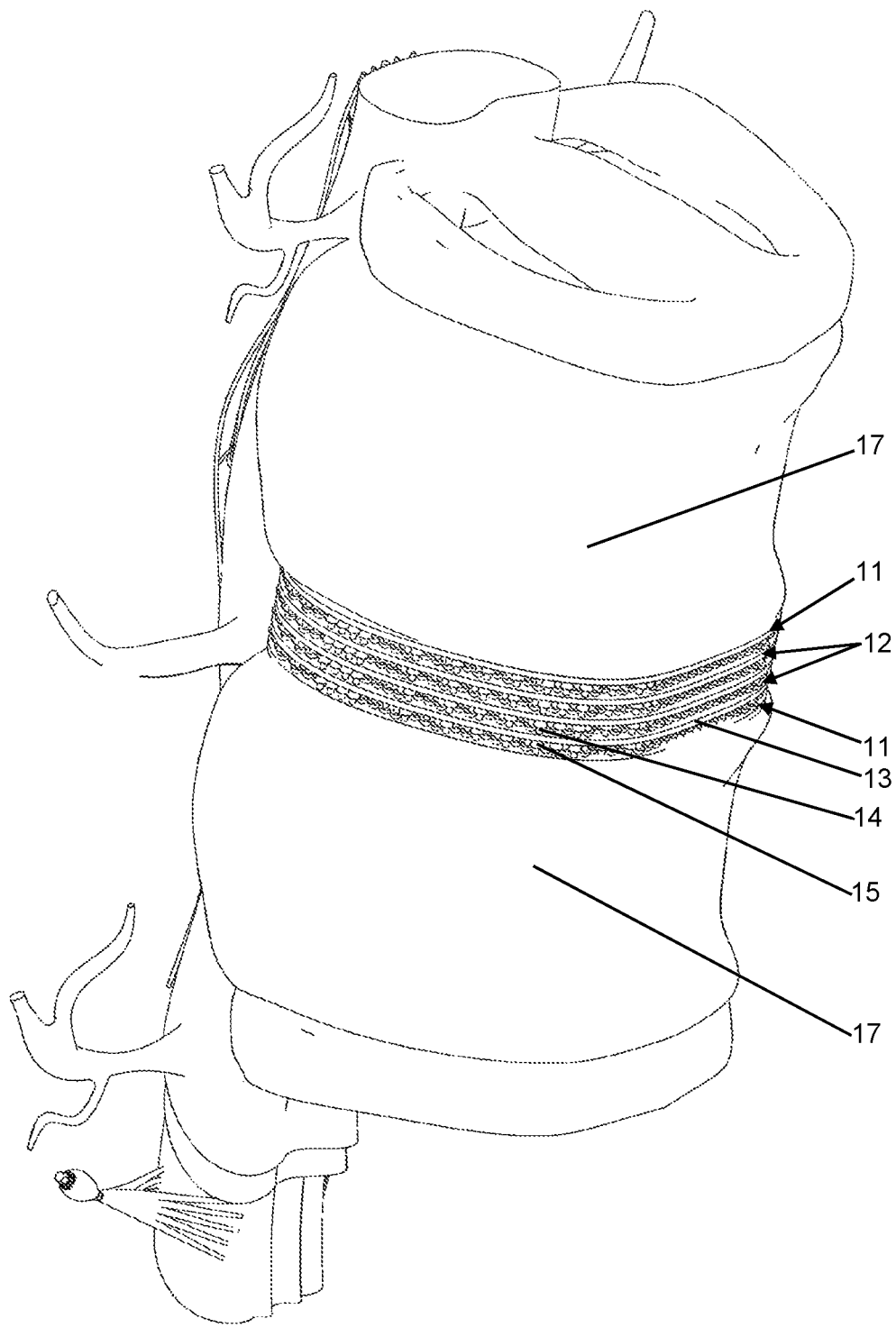
Figure 8:
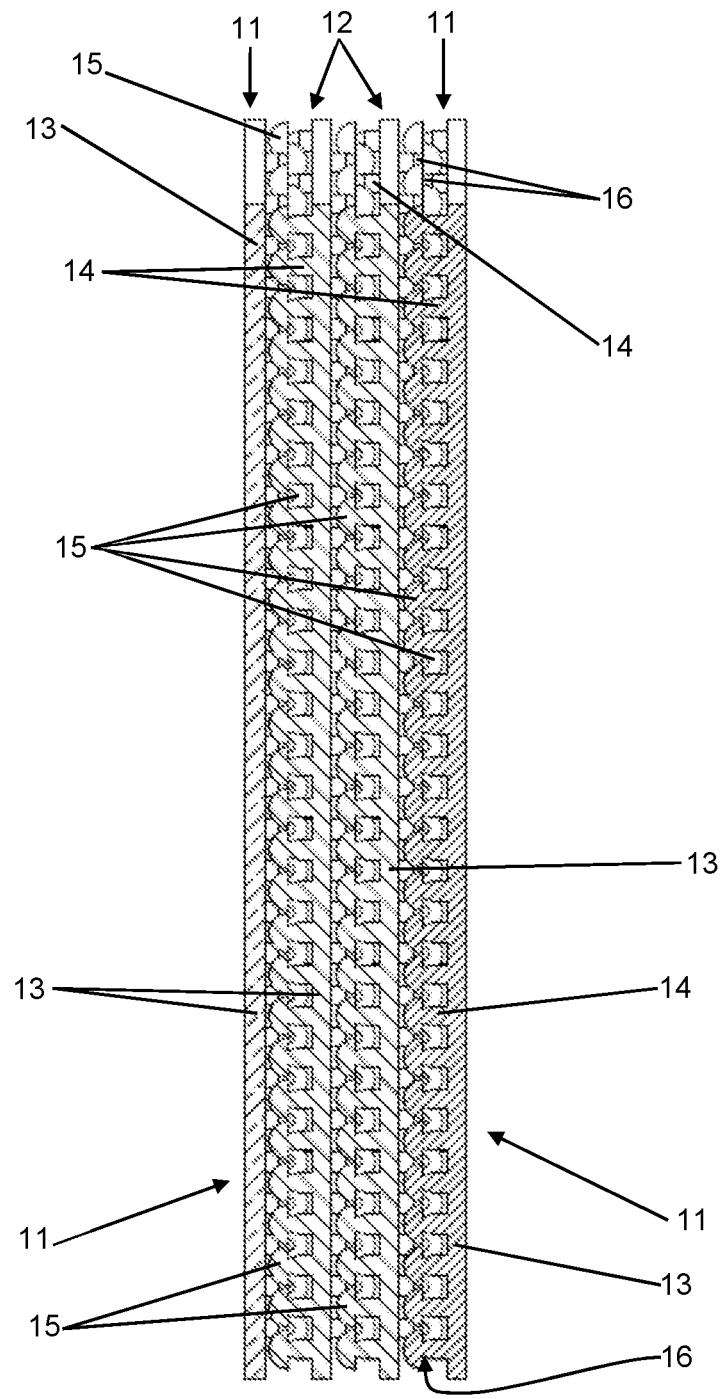

FIG. 5: shows a schematic cross-sectional view through two plates according to FIG. 2 that are not snapped in FIG. 6: shows a schematic perspective view onto a second cage according to the invention, which is constructed from four plates from a second kit according to the invention FIG. 7: shows a schematic perspective view of the cage according to FIG. 6, which is inserted between two vertebral bodies FIG. 8: shows a schematic cross-sectional view through the four snapped-in plates of the cage according to FIG. 6

Figure 9:
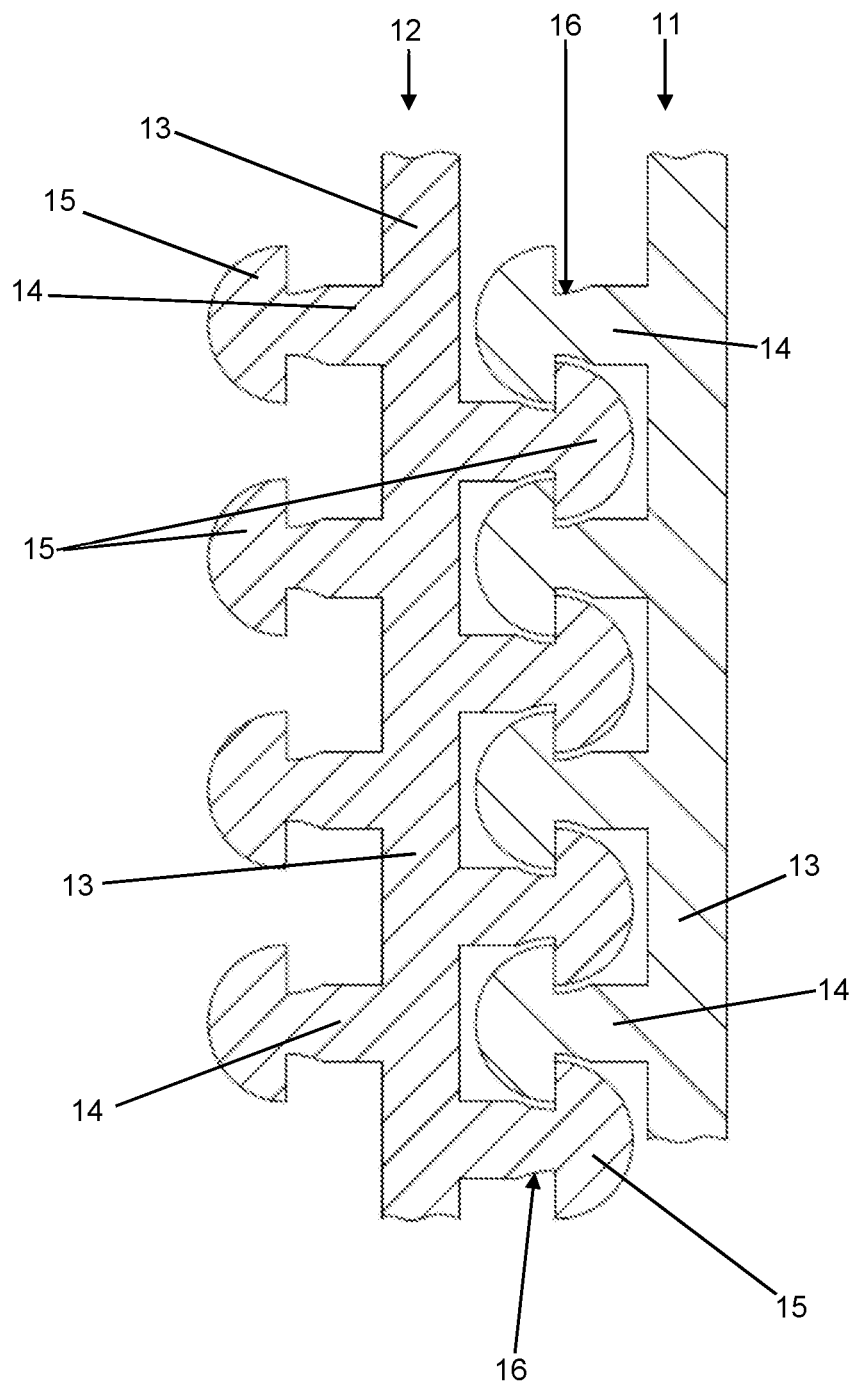

FIG. 9: shows an enlarged representation of a schematic cross-sectional view through two snapped-in plates from the kit according to FIGS. 6 to 8

Figure 10:
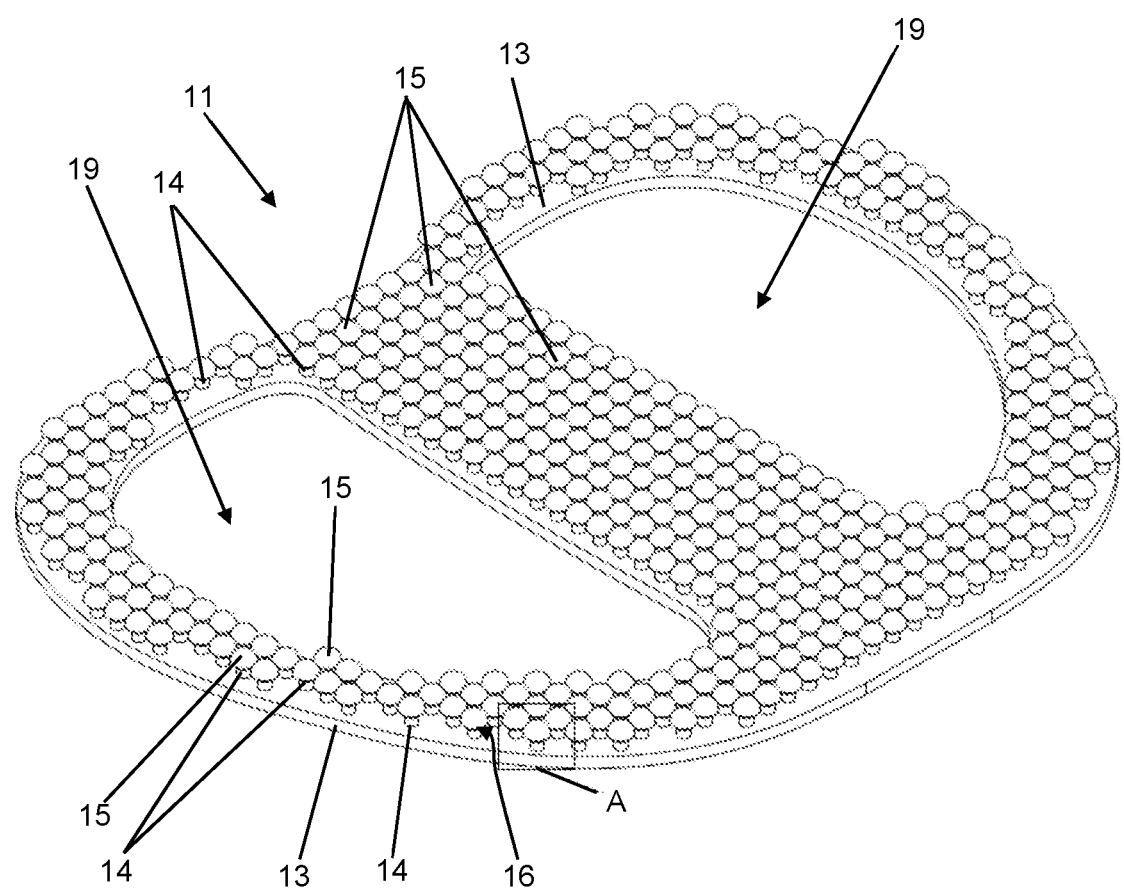

FIG. 10: shows a schematic perspective view onto one of the plates according to one of FIGS. 6 to 9

Figure 11:
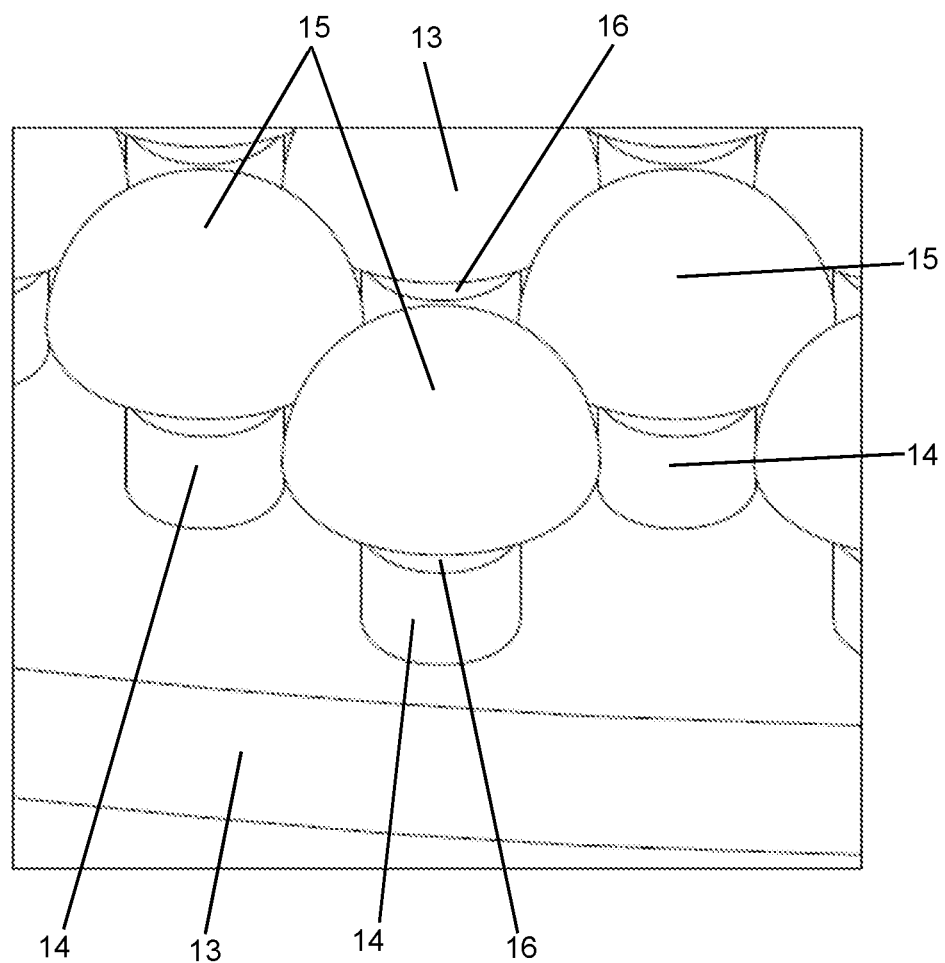

FIG. 11: shows an enlargement of a partial area A in FIG. 10

Figure 12:
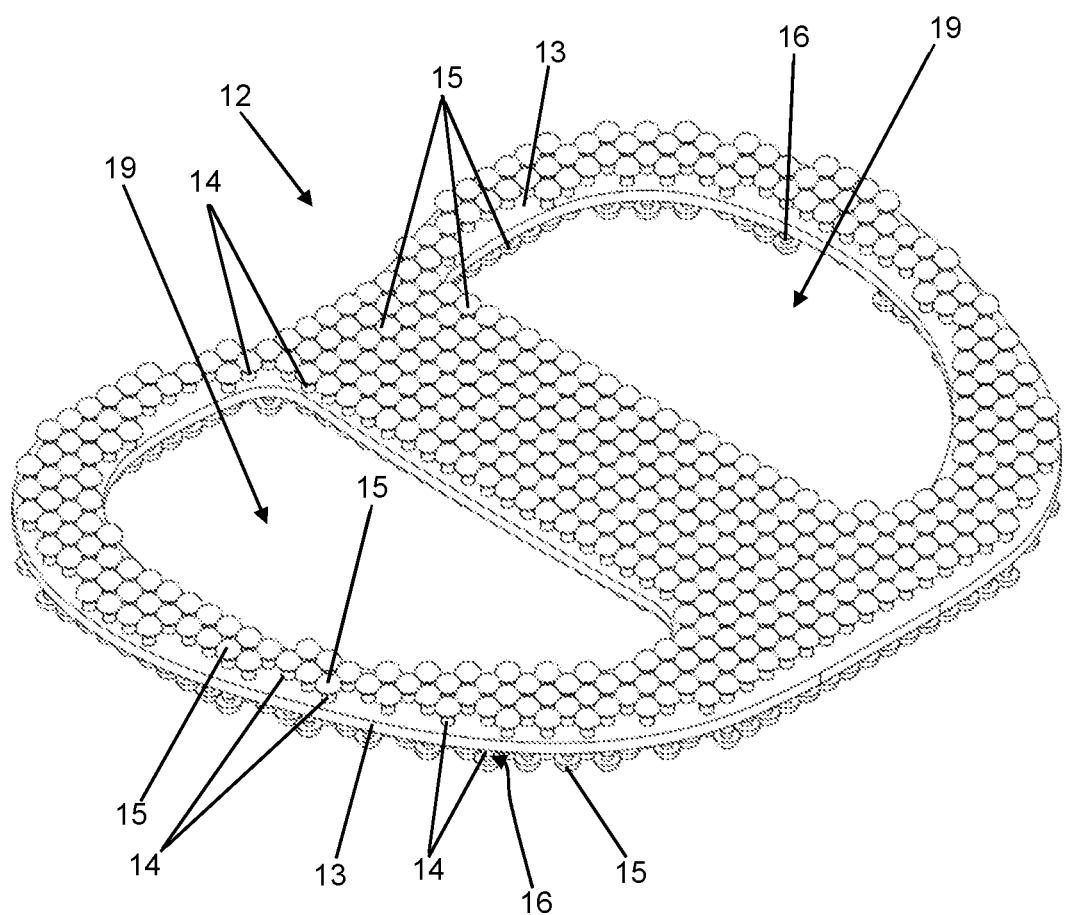

FIG. 12: shows a schematic perspective view onto one of the plates according to one of FIGS. 6 to 9

Figure 13:
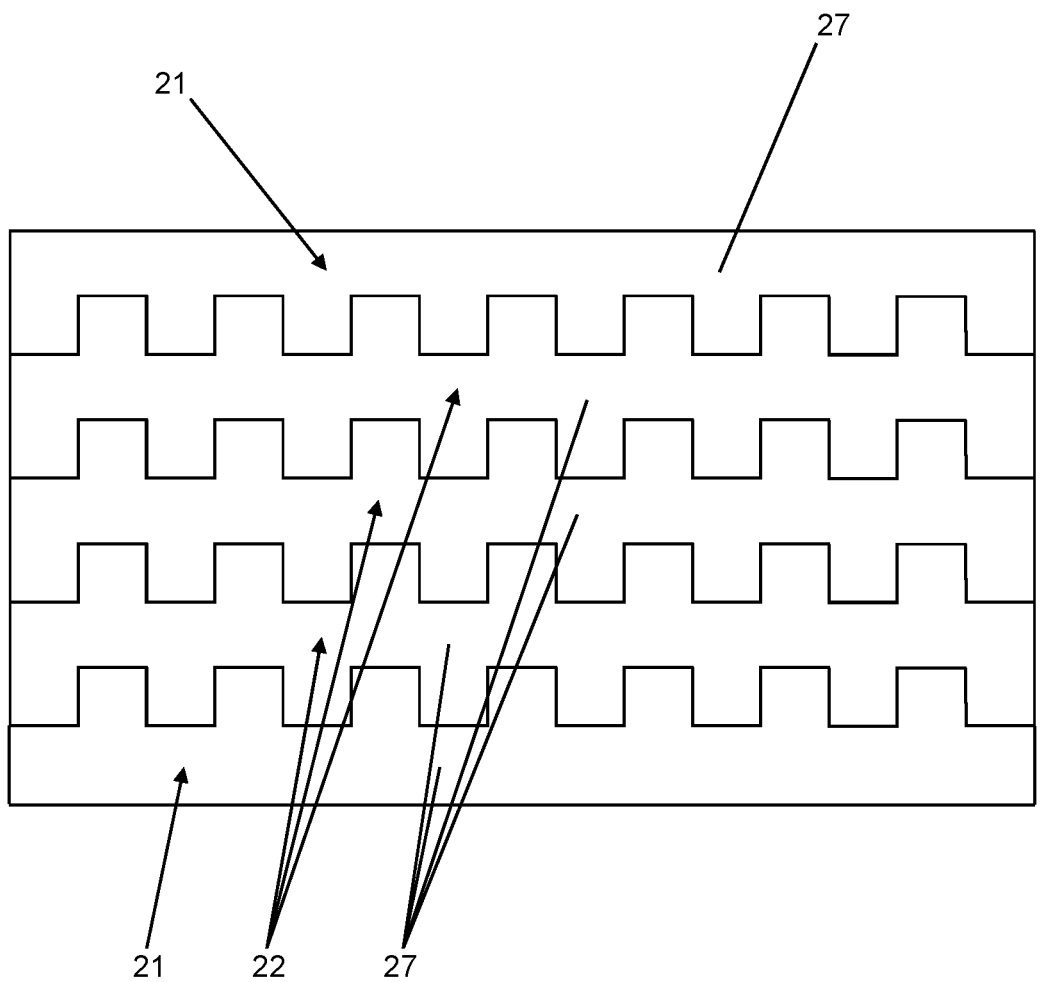
Figure 14:
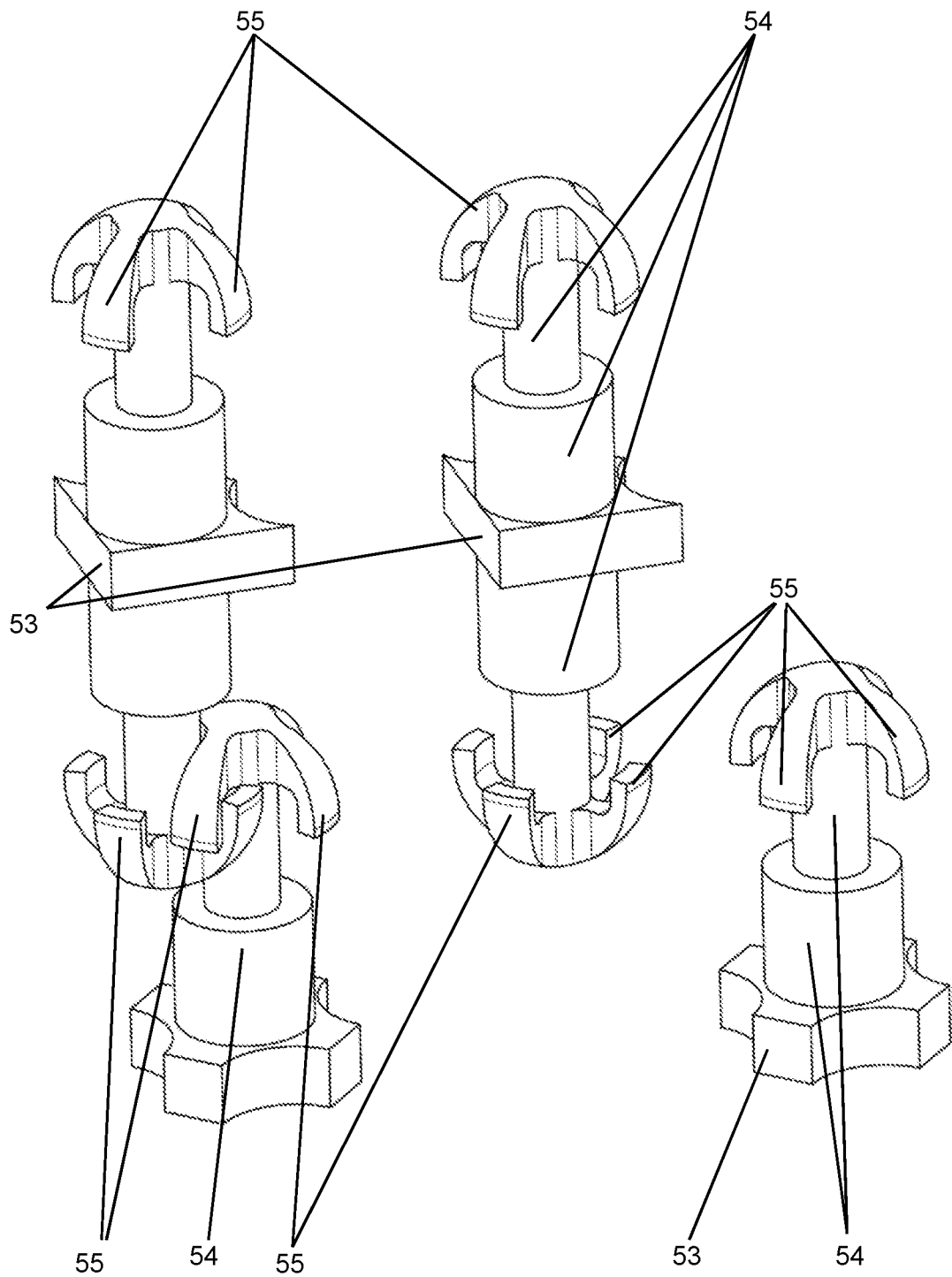
Figure 15:
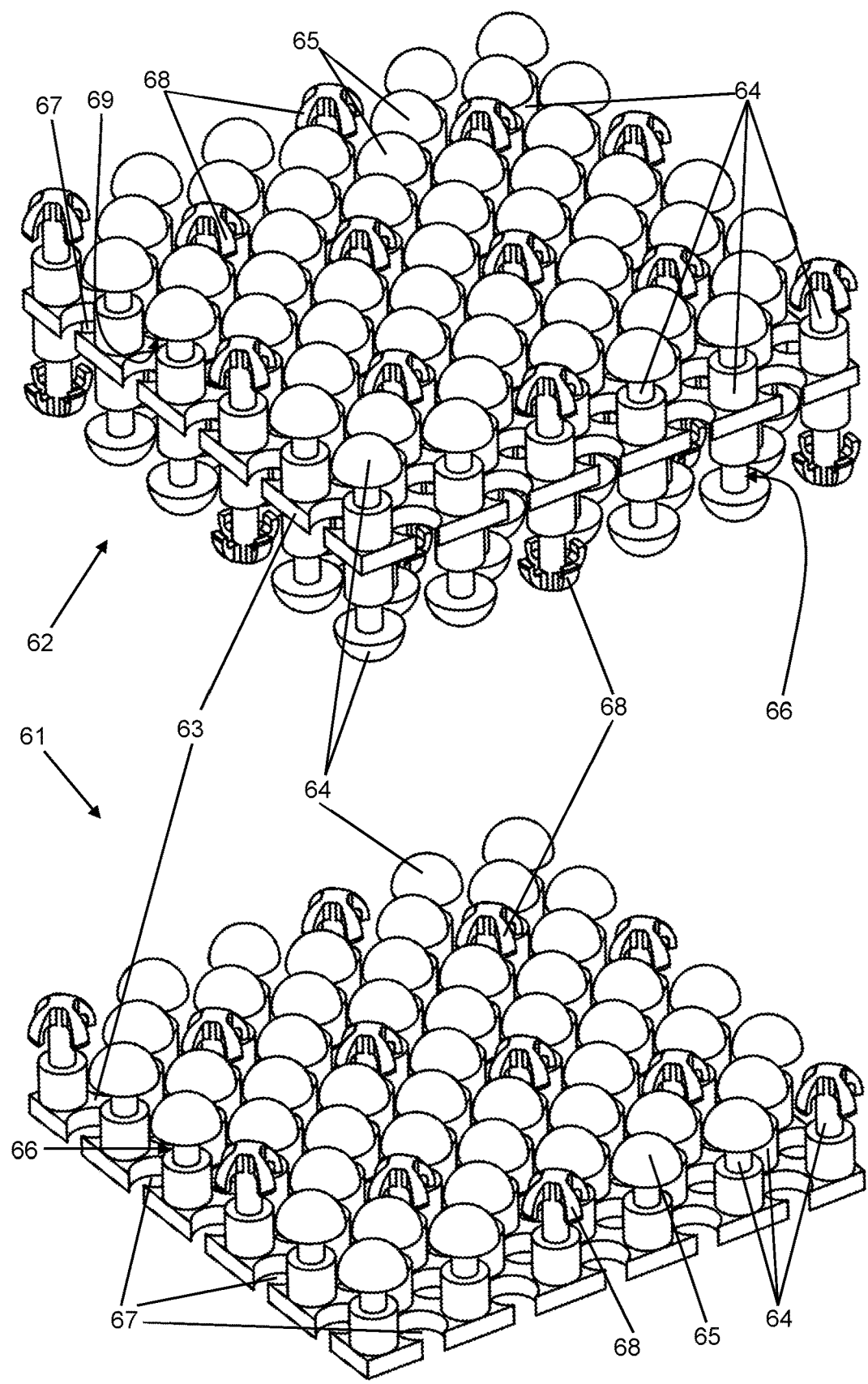
Figure 16:
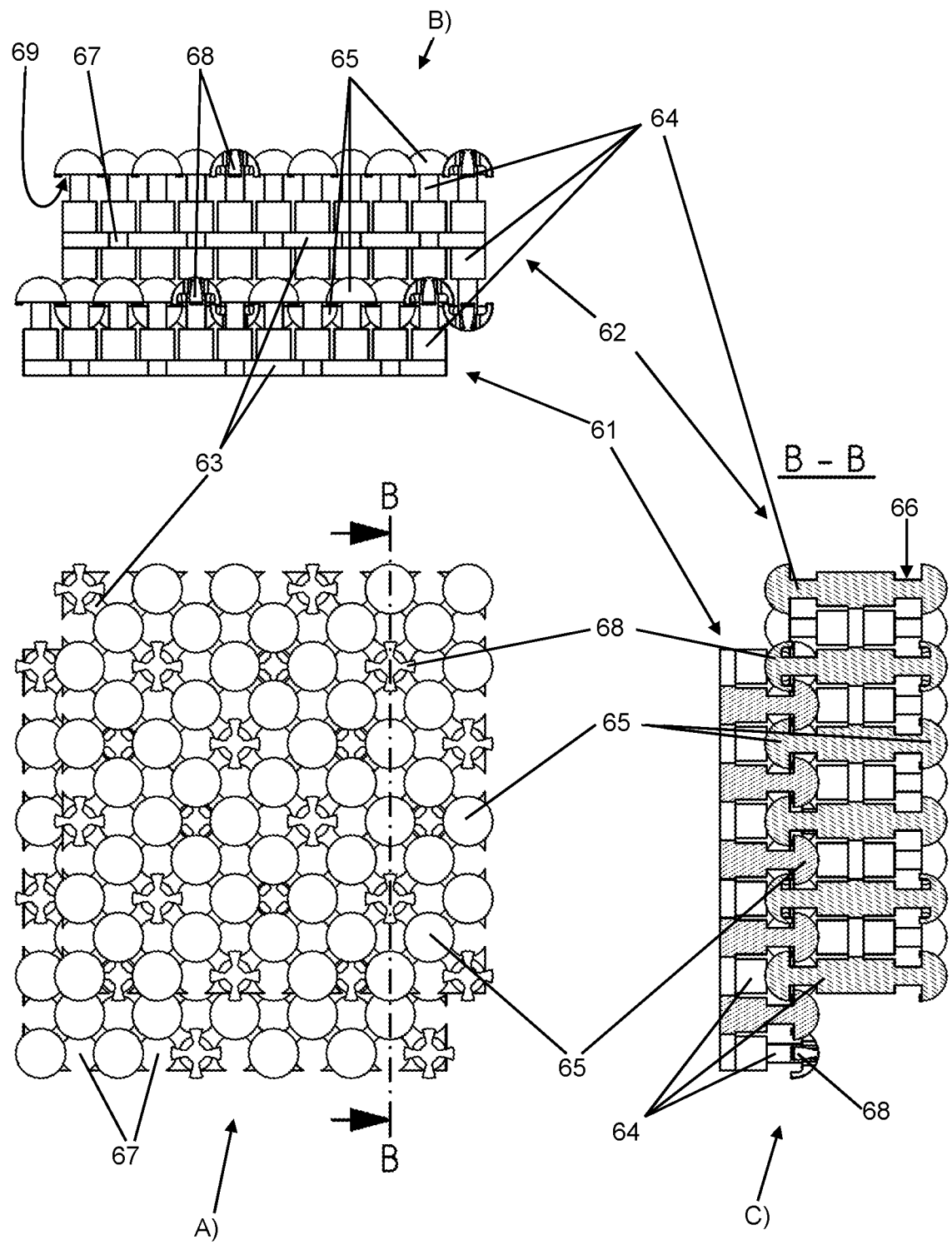
Figure 17:
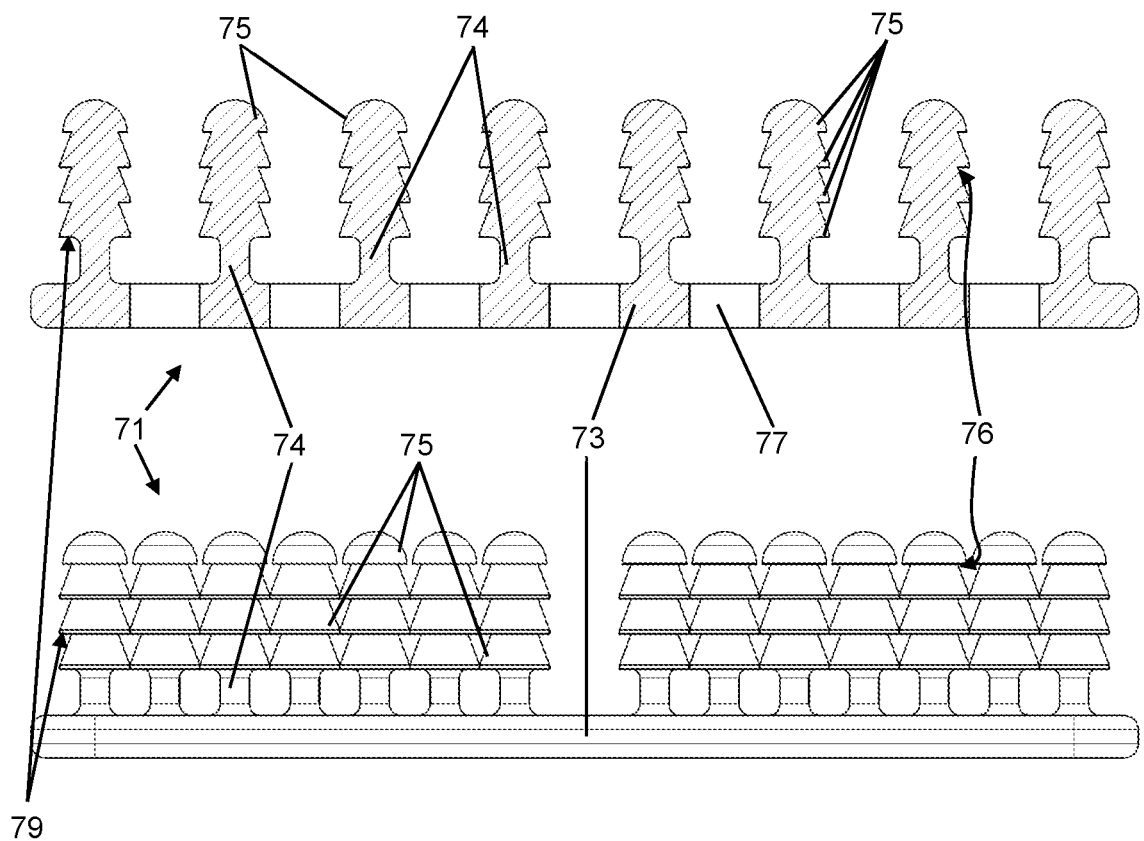

FIG. 13: shows a schematic side view onto five plates that are interlocked on the edge, which form a third cage according to the invention FIG. 14: shows a schematic perspective detailed view onto two interlocked hooks (left) and two hooks that are not interlocked (right) as parts of plates from a fourth kit according to the invention FIG. 15: shows a schematic perspective view onto sections of two plates that are not interlocked from a fifth kit according to the invention FIG. 16: shows three schematic views of the sections of two plates (according to FIG. 15) which are not connected to each other from the fifth kit A) Top view onto the upper side, B) Side view, C) Cross-sectional view along the section B-B according to FIG. 16 A FIG. 17: FIG. 17 above: a schematic cross-sectional view through an outer plate from a sixth kit according to the invention, and FIG. 17 below: a schematic side view onto the outer plate from the sixth kit FIG. 18: an enlarged representation of a schematic cross-sectional view through two snapped-in plates from the sixth kit according to FIG. 17

Figure 19:
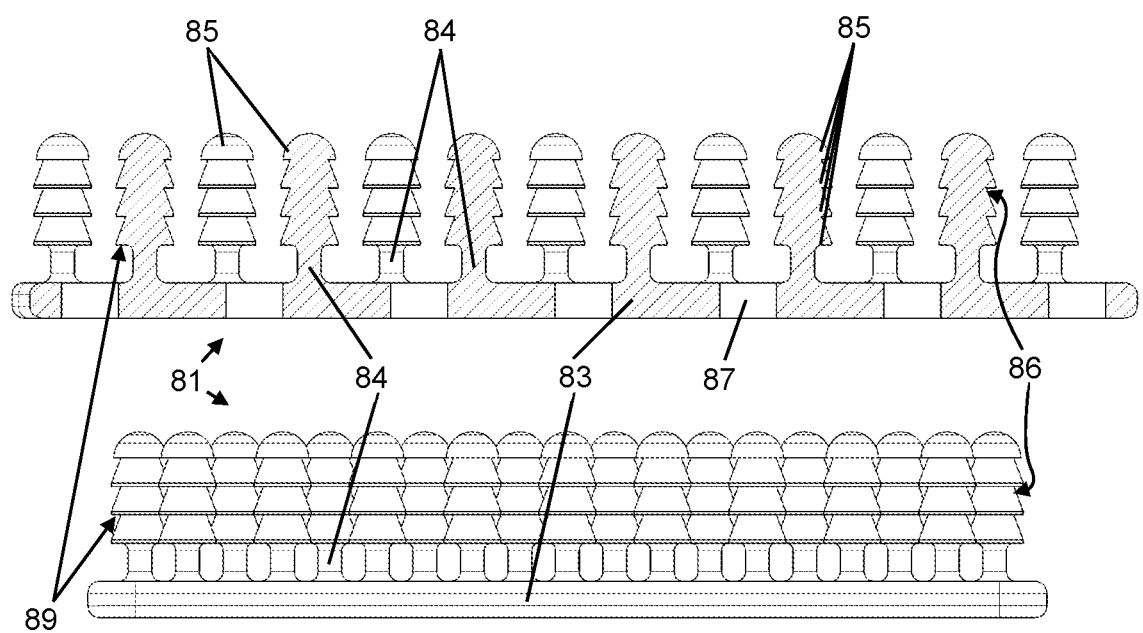

FIG. 19: FIG. 19 above: a schematic cross-sectional view through an outer plate from a seventh kit according to the invention, and FIG. 19 below: a schematic side view onto the outer plate from the seventh kit FIG. 20: an enlarged representation of a schematic cross-sectional view through two snapped-in plates from the seventh kit according to FIG. 19

Figure 21:
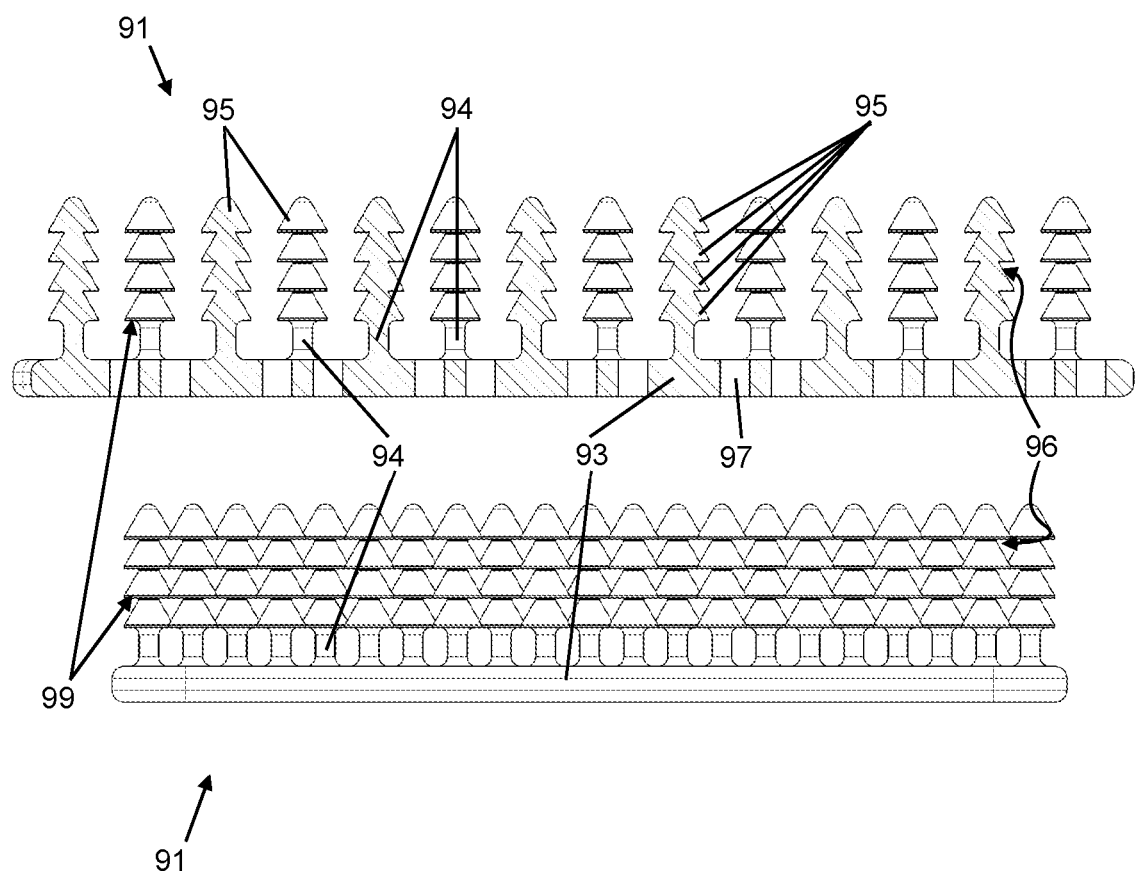

FIG. 21: FIG. 21 above: a schematic cross-sectional view through an outer plate from an eighth kit according to the invention, and FIG. 21 below: a schematic side view onto the outer plate of the eighth kit, and FIG. 22: an enlarged representation of a schematic cross-sectional view through two snapped-in plates from the eighth kit according to FIG. 21.

FIGS. 1 to 5 show a first embodiment of the present invention, with FIG. 1 showing a schematic perspective view onto a cage according to the invention which is constructed from five plates 1, 2 from a kit according to the invention, FIG. 2 shows a schematic perspective view onto two of the plates 1, 2 according to FIG. 1 which are not snapped-in to each other, FIG. 3 shows a schematic cross-sectional view through the five snapped-in plates 1, 2 of the cage according to FIG. 1, FIG. 4 shows an enlarged representation of a schematic cross-sectional view through the five snapped-in plates 1, 2 of the cage according to FIG. 1, and FIG. 5 shows a schematic cross-sectional view through the two plates according to FIG. 2 which are not snapped in.

The kit comprises at least two outer plates 1, which are provided to be fixed to vertebral bodies of the spine (not shown), and comprises several middle or inner plates 2, which can be inserted in between the outer plates 1 for setting the height of the cage. The plates 1, 2 consist of an elastic biocompatible plastic material or of stainless steel, titanium, a titanium alloy, tantalum, a tantalum alloy, but can also be fabricated from composites of said materials. The plates 1, 2 are manufactured by a CAM procedure (CAM—computer-aided manufacturing) and/or a 3D printing procedure, for example by selective laser melting, or SLM. Other rapid prototyping methods and/or computer-aided generative production methods can also be used for producing the plates 1, 2, such as, for example, Fused Layer Modeling/Manufacturing (FLM), Fused Deposition Modeling (FDM), Laminated Object Modelling (LOM) of plastic films, Layer Laminated Manufacturing (LLM) of plastic films, Electron Beam Melting (EBM) of plastic materials or metals, Multi Jet Modeling (MJM) of plastic materials, Selective Laser Sintering (SLS) of plastic materials or metals, Stereolithography (STL or SLA) of plastic materials, polishing or multi-axes milling procedures or Digital Light Processing (DLP) of photopolymerising liquid plastic materials.

The plates 1, 2 respectively comprise a plate-shaped planar structure 3, which bears all the plates 1, 2 and connects them. The planar structure 3 can be flexible and elastically deformable to a limited degree, so that other surfaces can also be formed as planes with the planar structure 3, so that the plates 1, 2 can to a small degree be adapted to the form of the vertebral bodies. From the planar structures 3, with each plate 1, 2, a plurality of pins 4 extend which stand up vertically from the plane of the planar structures 3.

In FIGS. 1 to 5, two different types of plates 1, 2 are shown, namely outer plates 1, which comprise a flat underside and with which the pins 4 only extend on one side of the planar structures 3 originating from the planar structure 3, and secondly, middle plates 2 and/or inner plates 2, with which the pins 4 extend originating from both sides of the planar structure 3. With a completed cage (see FIGS. 1, 3 and 4), the plates 1, 2 are arranged in a sandwich-like manner in relation to each other, wherein the outer plates 1 form the two covering surfaces and the inner plates 2 are arranged between the outer plates 1. The outer plates 1 can be affixed lying over a large surface on the vertebral bodies to be treated. For this purpose, eyelets (not shown) can be provided in the planar structure 3, so that the outer plates 1 can be bolted onto the vertebral bodies, or on the side of the planar structure 3 without pins 4, peaks (not shown) can be provided which are inserted into the bone of the vertebral bodies. The inner plates 2 can however theoretically also be affixed to the vertebral bodies to be treated, albeit with a lesser contact surface, so that theoretically, the outer plates 1 can be omitted.

On the otherwise cylindrical pins 4, on the ends of the pins 4 positioned opposite the planar structures 3, mushrooms 5 are provided as latching elements 5. The mushrooms 5 are rounded outwards (pointing away from the planar structure 3) and form spherical segments. However, other roundings are also possible, such as elliptical segments. On the side oriented towards the planar structure 3, the mushrooms 5 form a planar engagement surface, which are suitable for interlocking and snapping in with other mushrooms 5 on engaging plates 1, 2.

In the pins 4, grooves 6 are provided as counter snap-in elements adjacent to the mushrooms 5 and/or to the engagement surfaces, into which the mushrooms 5 of adjacent plates 1, 2 can engage and/or snap in. For this purpose, edges of the grooves 6 which face towards the planar structure 3 have a rounded shape, so that the mushrooms 5 can fit and/or snap in well to the grooves 6. The shape of the grooves 6 corresponds to a negative of the shape of the surface of the mushrooms 5, so that said mushrooms can come into contact along a line in one of the grooves 6. The mushrooms 5 thus form latching elements 5 and the grooves 6 form the matching counter snap-in elements 6. A further pushing in of the plates 1, 2 following the snap-in connection is prevented by this structure.

In this relation, FIGS. 3 and 4 show a schematic cross-sectional view onto plates 1, 2 of the kit according to the invention which are snapped in to each other via the mushrooms 5.

In the planar structure 3 of the outer plates 1, a plurality of continuous pores 7 is arranged between the pins 4, which create an open porosity of the cage on the contact surface to the vertebral bodies in a direction vertical to the planar structures 3. As a result, the bone of the vertebral bodies can grow together more easily with the outer plates 1 of the cage.

The pins 4 with the mushrooms 5 can be arranged in groups and/or islands of pins 4 and/or mushrooms 5 (not shown in FIGS. 1 to 5). As a result, pins 4 arranged on the edge of the groups and/or islands are easier to bend outwards when the mushrooms 5 of another plate 1, 2 are pressed on. Thus the plates 1, 2 are easier to connect to each other, since the elastic deformations of the pins 4 do not hinder each other when the mushrooms 5 are snapped into the grooves 6.

In order to construct a cage according to the invention with the aid of a kit according to the invention, the plates 1, 2 are preferably provided in contact with each other, but are not interlocked or snapped in to each other, so that thus the mushrooms 5 of the pins 4 of adjacent plates 1, 2 do not yet engage in each other. Additionally, the plates 1, 2 can be provided moistened with a fluid. The fluid preferably contains at least one pharmaceutically active substance which is suitable for combating an infection or stimulating bone growth. Alternatively or in addition, the plates 1, 2 can be coated with a pharmaceutically active substance of this type.

The cage can be formed by pressing the plates 1, 2 into each other via their surfaces. As a result, the plates 1, 2 snap into each other and the cage is rigidified in the desired form. Prior to or during this process, the plates 1, 2 can be deformed through a slight elastic deformation of the planar structures 3 and adapted to the treatment situation. After snapping into at least one further (usually then also deformed) inner plate 2, the two plates 1, 2 thus connected to each other stabilise mutually, so that the selected form is rigidified.

The plates 1, 2 can here snap into each other when the mushrooms 5 elastically deform the pins 4 of connected plates 1, 2 and through the elastic resilience of the pins 4, the mushrooms 5 and/or the edges of the mushrooms 5 press into the grooves 6 and as a result limit the movement of adjacent plates 1, 2 away from the planar structure 3 (see FIGS. 3 and 4). Due to the adapted form of the grooves 6 to the mushrooms 5, a further movement of the mushrooms 5 is blocked, in particular when a large number of mushrooms 5 is snapped into a large number of grooves 6.

Preferably, the dimensions of the mushrooms 5, the thickness of the planar structure 3, the shape of the grooves 6 and the length of the pins 4 between the planar structure 3 and the mushrooms 5 are coordinated with each other in such a manner that when the plates 1, 2 are connected the surfaces of the mushrooms 5 facing away from the planar structure 3 are in contact with the surface of the grooves 6 of adjacent plates 1, 2 and/or when the plates 1, 2 are connected, the engagement areas of the mushrooms 5 come into contact with the engagement areas of the mushrooms 5 of the adjacent plates 1, 2. As a result, it is achieved that the connected plates 1, 2 are not and/or not without a great force effect able to move against each other.

The grooves 6 also prevent the engagement areas or the opposite upper sides of the caps of the mushrooms 5 from completely covering the pores 7. In order for the recesses 7 to be even less covered by the mushrooms 5, the recesses 7 can comprise several slits (not shown) which are distributed over the extent of the recesses 7.

The completed cage comprises two open axial hollow chambers 8, which are created by positioning the plates 1, 2 one on top of the other, in which suitably fitting recesses 9 are provided. The open axial hollow chambers 8 and thus the recesses 9 serve to ensure that bones from the vertebral bodies can grow through them. For this purpose, the surfaces of the open axial hollow chambers 8 and of the recesses 9 are filled with autologous bone replacement material and, if desired, are additionally coated with a substance which promotes bone growth. The free profile of the recesses 9 and of the open axial chambers 8 totals approximately 10 mm, but at least 5 mm, so that the bone of the vertebral bodies can grow in well. The open axial hollow chambers 8 thus form the interior of the cage.

In order to ensure that the open axial hollow chambers 8 are uniform and that the outer form of the cage is even, the plates 1, 2 must be snapped in onto each other flush and/or so that they fit. In order to facilitate this, four positioning pins 10 respectively are provided as positioning aids 10 on the planar structures 3 of the outer plates 1. Accordingly, in addition the inner plates 2 comprise four matching bore holes in the planar structures 3 so that the positioning pins 10 are inserted through said bore holes when the plates 1, 2 snap into each other and thus specify the orientation and position of the inner plates 2 relative to the outer plate 1. As a result, it can be ensured that the plates 1, 2 are placed onto each other flush and/or in such a manner that they fit. The plates 1, 2 all have the same shape in relation to the plane of the planar structures 3, so that they can be laid one on top of the other in such a manner that they fit. With the embodiment shown in FIGS. 1 to 5, the length of the positioning pins 10 is selected precisely so that it reaches only through the bore hole of the adjacent plate 2. However, it would easily be possible to provide longer positioning pins 10 which extend through the bore holes of further plates 1, 2. Equally, the positioning pins 10 could also be provided on an inner plate 2 and bore holes could be provided in the outer plates 1. The positioning pins 10 could then also end in peaks which are inserted into the vertebral body and affixed there. Equally, with this variant (not shown), the positioning pins 10 can extend vertically from the planar structure 3 in both directions.

FIGS. 6 to 12 show a second embodiment of the present invention, whereby FIG. 6 shows a schematic perspective view onto a second cage according to the invention, which is constructed of four plates 11, 12 from a second kit according to the invention, FIG. 7 shows a schematic perspective view of the cage according to FIG. 6 in the state as used in the patient, FIG. 8 shows a schematic cross-sectional view through the four snapped-in plates 11, 12 of the cage according to FIG. 6, FIG. 9 shows an enlarged representation of a schematic cross-sectional view through two snapped-in plates 11, 12 from the kit according to FIGS. 6 to 8, FIG. 10 shows a schematic perspective view onto an outer plate 11 according to one of FIGS. 6 to 9, FIG. 11 shows an enlargement of a partial area A in FIG. 10, and FIG. 12 shows a schematic perspective view onto one of the inner plates 12 according to one of FIGS. 6 to 9.

The kit comprises at least two outer plates 11, which are provided for affixing to dorsal vertebral bodies 17 (see FIG. 7), and comprises several middle or inner plates 12 which can be inserted between the outer plates 11 in order to set the height of the cage. The plates 11, 12 consist of an elastic biocompatible plastic material or stainless steel, titanium, a titanium alloy, tantalum, a tantalum alloy or composites of said materials. The plates 11, 12 are produced using a CAM method (Computer-Aided Manufacturing) and/or using a 3D printing method, for example with selective laser melting, or SLM. Other rapid prototyping methods and/or computer-aided generative production methods can also be used for producing the plates 11, 12, such as, for example, Fused Layer Modeling/Manufacturing (FLM), Fused Deposition Modeling (FDM), Laminated Object Modelling (LOM) of plastic films, Layer Laminated Manufacturing (LLM) of plastic films, Electron Beam Melting (EBM) of plastic materials or metals, Multi Jet Modeling (MJM) of plastic materials, Selective Laser Sintering (SLS) of plastic materials or metals, Stereolithography (STL or SLA) of plastic materials, polishing or multi-axes milling procedures or Digital Light Processing (DLP) of photopolymerising liquid plastic materials.

The plates 11, 12 respectively comprise a plate-shaped planar structure 13, which bears all the plates 11, 12 and connects them. The planar structure 13 can be flexible and elastically deformable to a limited degree, so that other surfaces can also be formed as planes with the planar structure 13, so that the plates 11, 12 can to a small degree be adapted to the form of the vertebral bodies. From the planar structures 13, with each plate 11, 12, a plurality of pins 14 extends which stand up vertically from the plane of the planar structures 13.

In FIGS. 6 to 12, two different types of plates 11, 12 are shown, namely outer plates 11, which comprise a flat underside and with which the pins 14 only extend on one side of the planar structures 13 originating from the planar structure 13, and secondly, middle plates 12 and/or inner plates 12, with which the pins 14 extend originating from both sides of the planar structure 13. With a completed cage (see FIGS. 6, 7 and 8), the plates 11, 12 are arranged in a sandwich-like manner in relation to each other, wherein the outer plates 11 form the two covering surfaces and the inner plates 12 are arranged between the outer plates 11. The outer plates 11 can be affixed lying over a large surface on the vertebral bodies 17 to be treated. For this purpose, eyelets (not shown) can be provided in the planar structure 13, so that the outer plates 11 can be bolted onto the vertebral bodies 17, or on the side of the planar structure 13 without pins 14, peaks (not shown) can be provided which are inserted into the bone of the vertebral bodies 17. The inner plates 12 can however theoretically also be affixed to the vertebral bodies to be treated, albeit with a lesser contact surface, so that theoretically, the outer plates 11 can be omitted.

On the otherwise cylindrical pins 14, on the ends of the pins 14 positioned opposite the planar structures 13, mushrooms 15 are provided as latching elements 15. The mushrooms 15 are rounded outwards (pointing away from the planar structure 13) and form spherical segments. However, other roundings are also possible, such as elliptical segments. On the side oriented towards the planar structure 13, the mushrooms 15 form a planar engagement surface, which are suitable for interlocking and snapping in with other mushrooms 15 on engaging plates 11, 12.

In the pins 14, grooves 16 are provided as counter snap-in elements adjacent to the mushrooms 15 and/or to the engagement surfaces, into which the mushrooms 15 of adjacent plates 11, 12 can engage and/or snap in. For this purpose, edges of the grooves 16 which face towards the planar structure 13 have a rounded shape, so that the mushrooms 15 can fit and/or snap in well to the grooves 16. The shape of the grooves 16 corresponds to a negative of the shape of the surface of the mushrooms 15, so that said mushrooms can come into contact along a line in one of the grooves 16. The mushrooms 15 thus form latching elements 15 and the grooves 16 form the matching counter snap-in elements 16. A further pushing in of the plates 11, 12 following the snap-in connection is prevented by this structure.

In this relation, FIGS. 8 and 9 show a schematic cross-sectional view onto plates 11, 12 of the kit according to the invention which are snapped in to each other via the mushrooms 15. No pores are arranged in the planar structure 13, in contrast to the first exemplary embodiment.

The pins 14 with the mushrooms 15 can be arranged in groups and/or islands of pins 14 and/or mushrooms 15 (not shown in FIGS. 1 to 5). As a result, pins 14 arranged on the edge of the groups and/or islands are easier to bend outwards when the mushrooms 15 of another plate 11, 12 are pressed on. Thus the plates 11, 12 are easier to connect to each other, since the elastic deformations of the pins 14 do not hinder each other when the mushrooms 15 are snapped into the grooves 16.

In order to construct a cage according to the invention with the aid of a kit according to the invention, the plates 11, 12 are preferably provided in contact with each other, but are not interlocked or snapped in to each other, so that thus the mushrooms 15 of the pins 14 of adjacent plates 11, 12 do not yet engage in each other. Additionally, the plates 11, 12 can be provided moistened with a fluid. The fluid preferably contains at least one pharmaceutically active substance which is suitable for combating an infection or stimulating bone growth. Alternatively or in addition, the plates 11, 12 can be coated with a pharmaceutically active substance of this type.

The cage can be formed by pressing the plates 11, 12 into each other via their surfaces. As a result, the plates 11, 12 snap into each other and the cage is rigidified in the desired form. Prior to or during this process, the plates 11, 12 can be deformed through a slight elastic deformation of the planar structures 13 and adapted to the treatment situation. After snapping into at least one further (usually then equally deformed) inner plate 12, the two plates 11, 12 thus connected to each other stabilise mutually, so that the selected form is rigidified.

The plates 11, 12 can here snap into each other when the mushrooms 15 elastically deform the pins 14 of connected plates 11, 12 and through the elastic resilience of the pins 14, the mushrooms 15 and/or the edges of the mushrooms 15 press into the grooves 16 and as a result limit the movement of adjacent plates 11, 12 away from the planar structure 13 (see FIGS. 8 and 9). Due to the adapted form of the grooves 16 to the mushrooms 15, a further movement of the mushrooms 15 is blocked, in particular when a large number of mushrooms 5 is snapped into a large number of grooves 16.

Preferably, the dimensions of the mushrooms 15, the thickness of the planar structure 13, the shape of the grooves 16 and the length of the pins 14 between the planar structure 13 and the mushrooms 15 are coordinated with each other in such a manner that when the plates 11, 12 are connected the surfaces of the mushrooms 15 facing away from the planar structure 13 are in contact with the surface of the grooves 16 of adjacent plates 11, 12 and/or when the plates 11, 12 are connected, the engagement areas of the mushrooms 15 come into contact with the engagement areas of the mushrooms 15 of the adjacent plates 11, 12. As a result, it is achieved that the connected plates 11, 12 are not and/or not without a great force effect able to move against each other.

The completed cage comprises two open axial hollow chambers 18, which are created by positioning the plates 11, 12 one on top of the other, in which suitably fitting recesses 19 which are provided. The open axial hollow chambers 18 and thus the recesses 19 serve to ensure that bones from the vertebral bodies 17 can grow through them. For this purpose, the surfaces of the open axial hollow chambers 18 and of the recesses 19 are filled with autologous bone replacement material and, if desired, are additionally coated with a substance which promotes bone growth. The free profile of the recesses 19 and of the open axial chambers 18 totals approximately 12 mm, but at least 5 mm, so that the bone of the vertebral bodies can grow in well. The open axial hollow chambers 18 thus form the interior of the cage.

In order to ensure that the open axial hollow chambers 18 are uniform and that the outer form of the cage is even, the plates 11, 12 must be snapped in onto each other flush and/or so that they fit. In order to facilitate this, in the same way as with the first exemplary embodiment positioning pins (not shown) can be provided as positioning aids. The plates 11, 12 all have the same shape in relation to the plane of the planar structures 13, so that they can be laid one on top of the other in such a manner that they fit.

FIG. 13 shows a schematic side view onto five interlocked plates 21, 22, which form a third cage according to the invention. The cage is constructed in the same way as one of the first two exemplary embodiments. In contrast to these exemplary embodiments, on the planar structures (not shown in FIG. 13) of the outer plates 21 and the inner plates 22, edges 27 are provided which run around on the outside. The edges 27 are in contact with each other in such a manner that they interlock when the plates 21, 22 are snapped into each other. As a result, the cage is closed to the outside, so that autologous bone material cannot penetrate outwards from the interior of the cage. The cage can be designed to be open-pore in the interior through pores in the plates 21, 22, so that the bones can grow through well without materials for this purpose being able to penetrate outwards from the interior of the cage.

FIG. 14 shows a schematic perspective detailed view onto two interlocked hooks 55 (left) and two hooks 55 that are not interlocked (right) as parts of plates from a fourth kit according to the invention The structure of the complete plates for this purpose is completed in the same way as the plates according to one of the previous exemplary embodiments, wherein instead of mushrooms, the hooks 55 are provided to connect the plates.

On the otherwise cylindrical pins 54, on the ends of the pins 54 positioned opposite the planar structures 53, hooks 55 are provided as latching elements 55. The hooks 55 are rounded outwards (pointing away from the planar structure 53) and form parts of spherical surfaces. However, other roundings are also possible, such as elliptical segments. On the side oriented towards the planar structure 53, the hooks 55 form undercuts, which are suitable for interlocking or snapping in with other hooks 55 on engaging plates.

The pins 54 are thinner and/or formed with a smaller profile (as grooves) in the area adjacent to the hooks 55 and/or to the undercuts of the hooks 55. The hooks 55 of adjacent plates can more easily engage and/or snap into the thinner areas.

With the present fourth embodiment, only hooks 55 are provided as latching elements 55. In order to build a cage according to the invention, the plates are used lying in contact with each other but not interlocked or snapped into each other, so that thus, the hooks 55 of the pins 54 of adjacent plates do not yet engage with each other. Additionally, the plates can be provided moistened with a fluid. The fluid preferably contains at least one pharmaceutically active substance which is suitable for combating an infection or stimulating bone growth. Alternatively or in addition, the plates can be coated with a pharmaceutically active substance of this type.

The cage can be formed by pressing the plates into each other via their surfaces. As a result, the plates interlock or snap into each other and the cage is rigidified in the desired shape.

Here, the plates connect in such a manner that free intermediate chambers remain between the plates that are connected to each other in the area of the pins 54 and the hooks 55, so that the cage formed from the plates is open-pore in the directions parallel to the plane of the plates. The plates have a profile and/or a thickness of approximately 5 mm, so that the remaining pores comprise a free profile in the range of approximately 0.5 mm. This profile is sufficient to enable bone material to develop and/or to grow into the pores. The cage with its open pores can thus be described as osteoconductive. The cage formed from the plates is therefore well suited for connection to the vertebral bodies.

The plates should be firmly pressed into each other so that the cage is dimensionally stable. The plates can here snap into each other in a first step whereby the hooks 55 elastically deform the pins 54 of connected plates and through the elastic resilience of the pins 54, the hooks 55 and/or peaks of the hooks 55 press into each other and as a result restrict the movement of adjacent plates away from the planar structure 53. It is thus achieved that the connected plates cannot be moved against each other without being deformed.

The fourth embodiment according to FIG. 14 therefore primarily differs from the embodiment according to FIGS. 1 to 12 in that hooks 55 are provided as latching elements 55.

FIG. 15 shows a schematic perspective view onto sections of two plates 61, 62 which are not interlocked, of a fifth kit according to the invention, and FIG. 16 shows three schematic views of sections of two plates (according to FIG. 15) which are connected to each other from the fifth kit A) as a top view onto the upper side, B) in a side view, C) in a cross-sectional view along section B-B according to FIG. 16 A).

The plates 61, 62 consist of a biocompatible metal, in particular of stainless steel, titanium or a titanium alloy, tantalum or a tantalum alloy, although they can also be made of an elastic biocompatible plastic material or a composite of such materials. The plates 61, 62 are produced using a CAM method and/or a 3D printing method, for example using selective electron beam melting (EBM). Other rapid prototyping methods and/or computer-supported generative production methods can also be used to produce the plates 61, 62.

The plates 61, 62 respectively comprise a plate-shaped planar structure 63, which bears all the plates 61, 62 and connects them. The planar structure 63 is elastically deformable, so that other surfaces can also be formed as planes with the planar structure 63. From the planar structures 63, with each plate 61, 62, a plurality of pins 64 extend which stand up vertically from the plane of the planar structures 63. In the planar structure 63, a plurality of continuous pores 67 is arranged between the pins 64, which, when the plates 61, 62 are connected to each other to form a cage, can create an open porosity of the cage in a direction vertical to the planar structures 63 when the adjacent plates 61, 62 are not in contact, thus covering the pores 67.

In FIGS. 15 and 16, two different types of plates 61, 62 are shown, namely first, one outer plate 61, which comprise a flat underside and with which the pins 64 only extend on one side of the planar structures 63 originating from the planar structure 63, and secondly, inner plates 62, with which the pins 64 extend originating from both sides of the planar structure 63. The outer plates 61 are shown below in FIG. 15, in FIG. 16 A) below (on the image plane), in FIG. 16 B) below and in FIG. 16 C) on the left. The inner plates 61 are shown on top in FIG. 15, in FIG. 16 A) above (out of the image plane), in FIG. 16 B) above and in FIG. 16 C) on the right. The outer plates 61 can be affixed lying over a large surface on the vertebral bodies to be treated (not shown). The inner plates 62 can however also be affixed to the vertebral bodies to be treated, albeit with a lesser contact surface, so that theoretically, the outer plates 61 can be omitted.

On the otherwise cylindrical pins 64, on the ends of the pins 64 positioned opposite the planar structures 63, mushrooms 65 or groups of four hooks 68 respectively are provided as latching elements 65, 68. The mushrooms 65 are rounded outwards (pointing away from the planar structure 63) and form spherical segments. However, other roundings are also possible, such as elliptical segments. The hooks 68 are rounded outwards likewise. On the side oriented towards the planar structure 63, the mushrooms 65 form a planar engagement surface 69, which are suitable for interlocking and snapping in with other mushrooms 65 and hooks 68 on engaging plates 61, 62. Accordingly, the hooks 68 form undercuts on the side oriented towards the planar structure 63, which are suitable for interlocking and snapping in with other mushrooms 65 and hooks 68 of engaging plates 61, 62.

In the pins 64, grooves 66 are provided as counter snap-in elements adjacent to the engagement surfaces 69 and adjacent to the hooks 68, into which the mushrooms 65 and hooks 68 of adjacent plates 61, 62 can engage and/or snap in. For this purpose, the grooves 66, in contrast to the grooves 66 shown, but preferred according to the invention, can be formed as a negative of the shape of the curve of the mushrooms 65 and/or the hooks 68, so that the mushrooms 65 and the hooks 68 fit well into the grooves 66.

With the present fifth embodiment, mushrooms 65 and hooks 68 are provided as a mixture on the plates 61, 62 as latching elements 65, 68, wherein two of eleven latching elements 65, 68 are hooks 68, and the remainder are mushrooms 65. This can also be reversed, and the hooks 68 and mushrooms 65 can also be present in another mixture ratio.

In order to build a cage according to the invention, the plates 61, 62 are used lying in contact with each other but not interlocked or snapped into each other (i.e. not as shown in FIG. 16), so that thus, the mushrooms 65 and hooks 68 of the pins 64 of adjacent plates 61, 62 do not yet engage with each other. Additionally, the plates 61, 62 can be provided moistened with a fluid. The fluid preferably contains at least one pharmaceutically active substance, in particular an autologous bone substance. Alternatively or in addition, the plates can be coated with a pharmaceutically active substance of this type.

The cage can be formed by pressing the plates 61, 62 into each other via their surfaces. As a result, the plates 61, 62 snap into each other and the cage is rigidified in the desired form. Prior to this process, the plates 61, 62 can also be deformed through elastic deformation of the planar structures 63 and adapted to the treatment situation. After interlocking or snapping into at least one further plate 61, 62, the two plates 61, 62 thus connected to each other stabilise mutually, so that the selected form is rigidified.

Here, the plates 61, 62 connect in such a manner that free intermediate chambers remain between the plates 61, 62 that are connected to each other in the area of the pins 64, the mushrooms 65, the hooks 68 and the grooves 66, so that the cage formed from the plates 61, 62 is open-pore in the directions parallel to the plane of the plates 61, 62. The plates 61, 62 have a profile and/or a thickness of approximately 9 mm, so that the remaining pores 67 comprise a free profile in the range of approximately 0.9 mm. This profile is sufficient to enable bone material to develop and/or to grow into the pores 67. The cage with its open pores 67 can thus be described as osteoconductive. The cage formed from the plates 61, 62 is therefore well suited for connection to the vertebral bodies.

The plates 61, 62 should be firmly pressed into each other so that the cage is dimensionally stable. The plates 61, 62 can here snap into each other whereby the mushrooms 65 and hooks 68 elastically deform the pins 64 of connected plates 61, 62 and through the elastic resilience of the pins 64, the mushrooms 65 and hooks 68 and/or the edges of the mushrooms 65 and peaks of the hooks 68 press into the grooves 66 and as a result restrict the movement of adjacent plates 61, 62 away from the planar structure 63 (see FIG. 16). It is also possible that first the edges of the mushrooms 65 and/or the peaks of the hooks 68 plastically deform the pins 64, the grooves 66 or the mushrooms 65 to a small degree and thus a snapped-in connection between the plates 61, 62 occurs.

Preferably, the dimensions of the mushrooms 65, of the hooks 68, the thickness of the planar structure 63, the shape of the grooves 66 and the length of the pins 64 between the planar structure 63 and the mushrooms 65 or hooks 68 are coordinated with each other in such a manner that when the plates 61, 62 are connected the surfaces of the mushrooms 65 and hooks 68 facing away from the planar structure 63 are in contact with the surface of adjacent plates 61, 62 and/or when the plates 61, 62 are connected, the surfaces of the mushrooms 65 and hooks 68 facing away from the planar structure 63 are in contact on the engagement surface 69 of the mushrooms 65 and preferably along at least one line or particularly preferably in a planar manner on the grooves 66 of the pins 64 of the adjacent plate 61, 62. As a result, it is achieved that the connected plates 61, 62 are not able to move against each other without being deformed.

The fifth embodiment according to FIGS. 15 and 16 thus primarily differs from that according to FIGS. 1 to 5 by the fact that hooks 68 are provided as latching elements 68.

Figure 18:
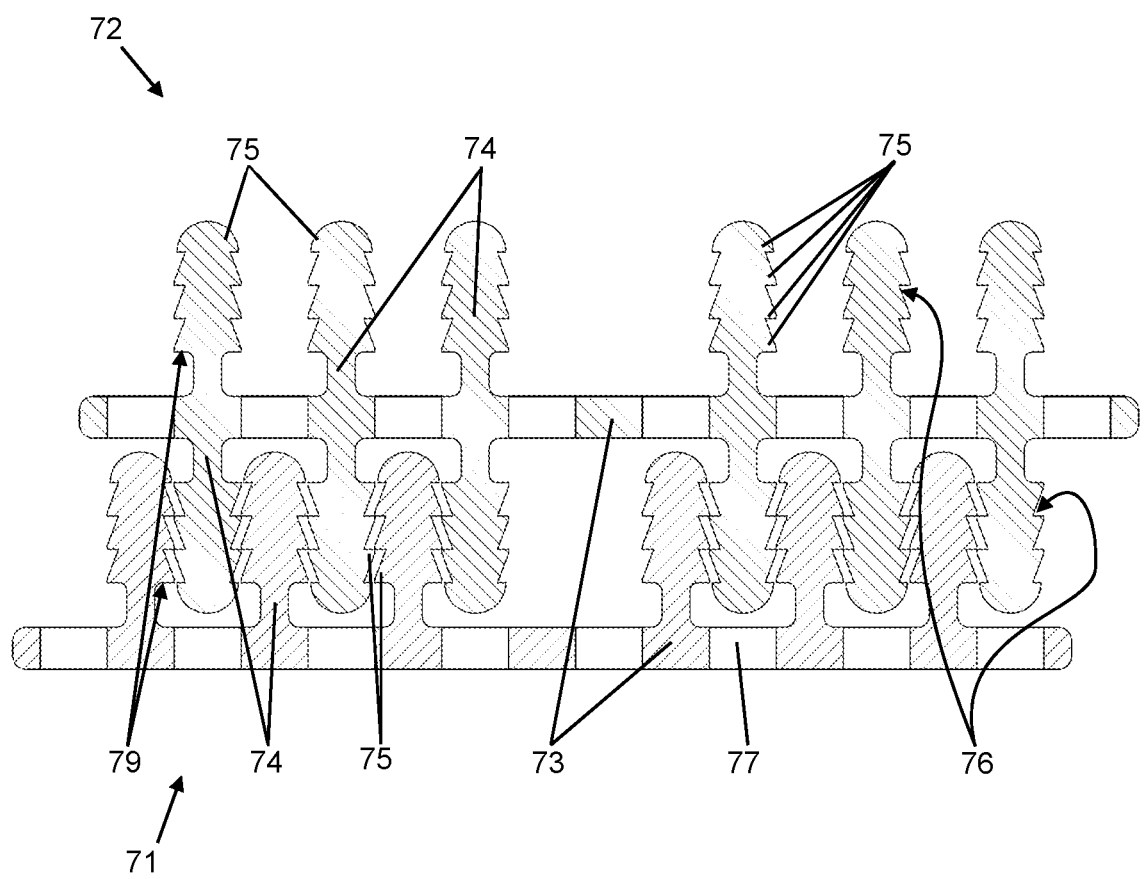

FIG. 17 shows a schematic cross-sectional view through an outer plate of a sixth kit according to the invention (FIG. 17, above), and a schematic side view onto the outer plate of the sixth kit (FIG. 17, below). In this regard, FIG. 18 shows an enlarged representation of a schematic cross-sectional view through two snapped-in plates of the sixth kit according to FIG. 17.

Figure 20:
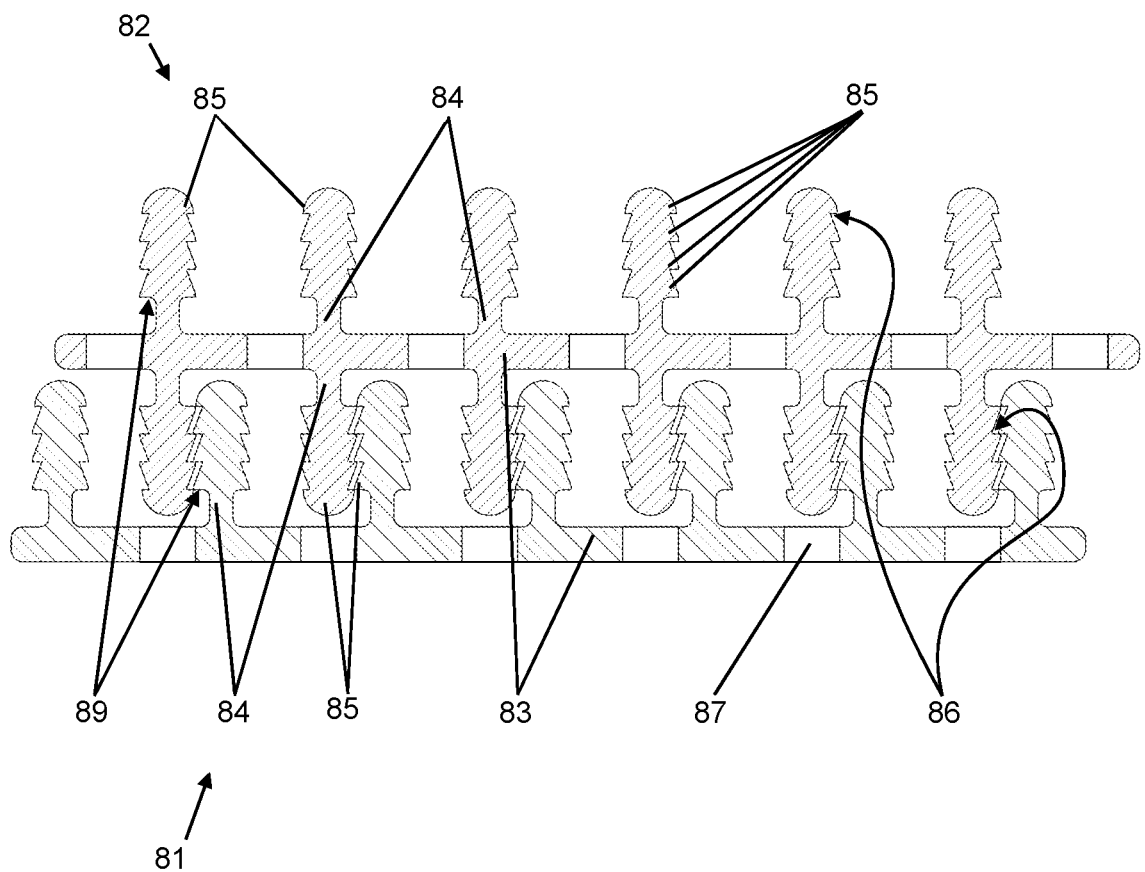

FIG. 19 shows a schematic cross-sectional view through an outer plate of a seventh kit according to the invention (FIG. 19, above) and a schematic side view onto the outer plate of the seventh kit according to the invention (FIG. 19, below). In this regard, FIG. 20 shows an enlarged representation of a schematic cross-sectional view through two snapped-in plates of the seventh kit according to FIG. 19.

Figure 22:
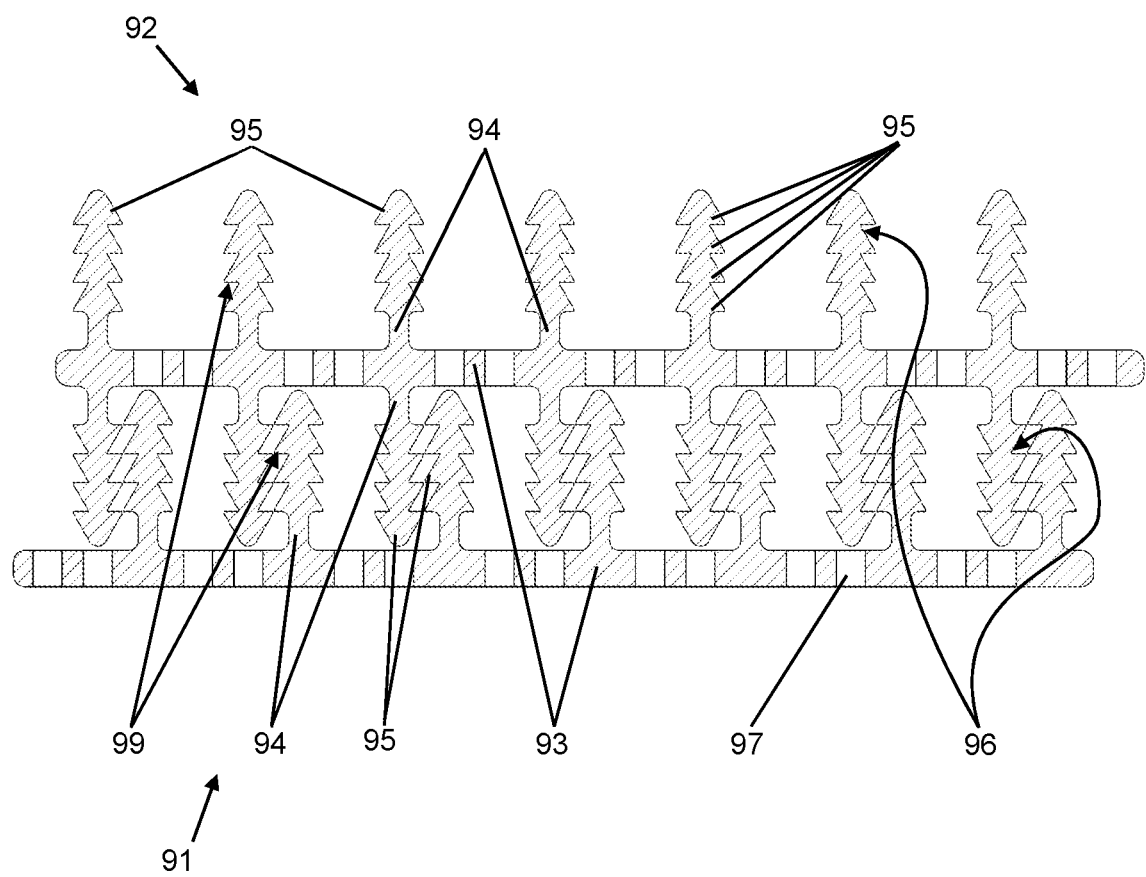

FIG. 21 shows a schematic cross-sectional view through an outer plate of an eighth kit according to the invention (FIG. 21, above) and a schematic side view onto the outer plate of the eighth kit according to the invention (FIG. 21, below). In this regard, FIG. 22 shows an enlarged representation of a schematic cross-sectional view through two snapped-in plates of the eighth kit according to FIG. 21.

These three embodiments, six, seven and eight, are highly similar to each other, and can thus be described collectively below.

The kits comprise at least two outer plates 71, 81, 91, which are provided for affixing to dorsal vertebral bodies, and which comprise several middle or inner plates 72, 82, 92, which can be inserted between the outer plates 71, 81, 91, in order to set the height of the cage. The plates 71, 72, 81, 82, 91, 92 consist of an elastic biocompatible plastic material or stainless steel, titanium, a titanium alloy, tantalum, a tantalum alloy or composites of said materials. The plates 71, 72, 81, 82, 91, 92 are produced using a CAM method (Computer-Aided Manufacturing) and/or using a 3D printing method, for example with selective laser melting, or SLM. Other rapid prototyping methods and/or computer-aided generative production methods can also be used for producing the plates 71, 72, 81, 82, 91, 92 such as, for example, Fused Layer Modeling/Manufacturing (FLM), Fused Deposition Modeling (FDM), Laminated Object Modelling (LOM) of plastic films, Layer Laminated Manufacturing (LLM) of plastic films, Electron Beam Melting (EBM) of plastic materials or metals, Multi Jet Modeling (MJM) of plastic materials, Selective Laser Sintering (SLS) of plastic materials or metals, Stereolithography (STL or SLA) of plastic materials, polishing or multi-axes milling procedures or Digital Light Processing (DLP) of photopolymerising liquid plastic materials.

The plates 71, 72, 81, 82, 91, 92 respectively comprise a plate-shaped planar structure 73, 83, 93, which bears all the plates 71, 72, 81, 82, 91, 92 and connects them. The planar structure 73, 83, 93 can be flexible and elastically deformable to a limited degree, so that other surfaces can also be formed as planes with the planar structure 73, 83, 93, so that the plates 71, 72, 81, 82, 91, 92 can to a small degree be adapted to the form of the vertebral bodies. From the planar structures 73, 83, 93, with each plate 71, 72, 81, 82, 91, 92, a plurality of pins 74, 84, 94 extend which stand up vertically from the plane of the planar structures 73, 83, 93.

In FIGS. 17 to 22, two different types of plates 71, 72, 81, 82, 91, 92 are shown respectively, namely outer plates 71, 81, 91, which comprise a flat underside and with which the pins 74, 84, 94 only extend on one side of the planar structures 73, 83, 93 originating from the planar structure 73, 83, 93, and secondly, middle plates 72, 82, 92 and/or inner plates 72, 82, 92, with which the pins 74, 84, 94 extend originating from both sides of the planar structure 73, 83, 93. With a completed cage and/or with conjoined or snapped-in plates 71, 72, 81, 82, 91, 92 (see FIGS. 18, 20 and 22), the plates 71, 72, 81, 82, 91, 92 are arranged in a sandwich-like manner in relation to each other, wherein the outer plates 71, 81, 91 form the two covering surfaces and the inner plates 72, 82, 92 are arranged between the outer plates 71, 81, 91. The outer plates 71, 81, 91 can be affixed lying over a large surface on the vertebral bodies to be treated. For this purpose, eyelets (not shown) can be provided in the planar structure 73, 83, 93, so that the outer plates 71, 81, 91 can be bolted onto the vertebral bodies, or on the side of the planar structure 73, 83, 93 without pins 74, 84, 94, peaks (not shown) can be provided which are inserted into the bone of the vertebral bodies. The inner plates 72, 82, 92 can however theoretically also be affixed to the vertebral bodies to be treated, albeit with a lesser contact surface, so that theoretically, the outer plates 71, 81, 91 can be omitted.

On the otherwise cylindrical pins 74, 84, 94, four mushrooms 75, 85, 95 are provided respectively as latching elements 75, 85, 95. The mushrooms 75, 85, 95 on the peaks of the pins 74, 84, 94 are rounded outwards (pointing away from the planar structure 73, 83, 93). With the sixth embodiment (FIGS. 17 and 18) and the seventh embodiment (FIGS. 19 and 20), the mushrooms 75, 85 form spherical segments on the peaks of the pins 74, 84, 94, while with the eleventh embodiment, the mushrooms 95 are somewhat more pointed on the peaks of the pins 94. However, other roundings are also possible, such as elliptical segments. The mushrooms 75, 85, 95 which are arranged below the mushrooms 75, 85, 95 on the peak of the pins 74, 84, 94, and which are thus arranged on the pins 74, 84, 94 between the planar structure 73, 83, 93 and the mushrooms 75, 85, 95, and the mushrooms 75, 85, 95 which are arranged on the side of the pins 74, 84, 94 facing away from the planar structure 73, 83, 93, have the shape of a truncated cone and/or are truncated cone-shaped. On the side oriented towards the planar structure 73, 83, 93, the mushrooms 75, 85, 95 form a planar engagement surface 79, 89, 99, which are suitable for interlocking and snapping in with other mushrooms 75, 85, 95 on engaging plates, or with recesses 76, 86, 96 of engaging plates. The pins 94 and the mushrooms 95 of the eighth embodiment (FIGS. 21 and 22) comprise a somewhat lesser diameter than those of the sixth and seventh embodiment, wherein the engagement surfaces 99 of the eighth embodiment are somewhat deeper and/or larger-area than the engagement surfaces 79, 89 of the sixth and seventh embodiment.

In the pins 74, 84, 94, and/or between the mushrooms 75, 85, 95, grooves 76, 86, 96 are provided as counter snap-in elements 76, 86, 96, into which the mushrooms 75, 85, 95 of adjacent plates 71, 72, 81, 82, 91, 92 can engage and/or interlock or snap in. The mushrooms 75, 85, 95 thus form latching elements 75, 85, 95 and the grooves 76, 86, 96 form approximately matching counter snap-in elements 76, 86, 96. With the sixth, seventh and eighth embodiment, the plates 71, 72, 81, 82, 91, 92 can be pushed in further by pushing the pins 74, 84, 94 with the mushrooms 75, 85, 95 into and/or through the recesses 73, 83, 93.

In this regard, FIGS. 18, 20 and 22 show a schematic cross-sectional view onto the plates 71, 72, 81, 82, 91, 92 of the kits according to the invention which are interlocked via the mushrooms 75, 85, 95. In the planar structures 73, 83, 93 of the outer plates 71, 72, 81, 82, 91, 92, a plurality of continuous pores 77, 87, 97 is arranged between the pins 74, 84, 94. The pores 74, 84, 94 create an open porosity of the cage on the contact surface to the vertebral bodies in a direction vertical to the planar structures 73, 83, 93. As a result, the bone of the vertebral bodies can grow together more easily with the outer plates 71, 81, 91 of the cage.

The pins 74, 84, 94 are thinnest between the mushrooms 75, 85, 95 and the planar structures 73, 83, 93, so that the pins 74, 84, 94 can most easily be bent over in the area of the connection to the planar structures 73, 83, 93, and/or are easiest to move there, in order to enable the snap-in process or interlocking of the mushrooms 75, 85, 95 with the grooves 76, 86, 96 between the mushrooms 75, 85, 95. In order to construct a cage according to the invention with the aid of a kit according to the invention, the plates 71, 72, 81, 82, 91, 92 are preferably provided in contact with each other, but are not interlocked or snapped in to each other, so that thus the mushrooms 75, 85, 95 of the pins 74, 84, 94 of adjacent plates 71, 72, 81, 82, 91, 92 do not yet engage in each other. Additionally, the plates 71, 72, 81, 82, 91, 92 can be provided moistened with a fluid. The fluid preferably contains at least one pharmaceutically active substance which is suitable for combating an infection or stimulating bone growth. Alternatively or in addition, the plates 71, 72, 81, 82, 91, 92 can be coated with a pharmaceutically active substance of this type.

The cage can be formed by pressing the plates 71, 72, 81, 82, 91, 92 into each other via their surfaces. As a result, the plates 71, 72, 81, 82, 91, 92 snap into each other and the cage is rigidified in the desired form. Prior to or during this process, the plates 71, 72, 81, 82, 91, 92 can also be deformed through a slight elastic deformation of the planar structures 73, 83, 93 and adapted to the treatment situation. After snapping into at least one further (usually then also deformed) inner plate 72, 82, 92, the two plates 71, 72, 81, 82, 91, 92 thus connected to each other stabilise mutually, so that the selected form is rigidified.

The plates 71, 72, 81, 82, 91, 92 can here snap into each other when the mushrooms 75, 85, 95 elastically deform the pins 74, 84, 94 of connected plates 71, 72, 81, 82, 91, 92 and through the elastic resilience of the pins 74, 84, 94, the mushrooms 75, 85, 95 and/or the edges of the mushrooms 75, 85, 95 press into the grooves 76, 86, 96 and as a result limit the movement of adjacent plates 71, 72, 81, 82, 91, 92 away from the planar structure 73, 83, 93 (see FIGS. 18, 20 and 22).

Here, the plates 71, 72, 81, 82, 91, 92 connect in such a manner that free intermediate chambers remain between the plates 71, 72, 81, 82, 91, 92 that are connected to each other in the area of the pins 74, 84, 94 the mushrooms 75, 85, 95 and the grooves 76, 86, 96, so that the cage formed from the plates 71, 72, 81, 82, 91, 92 is open-pore in the directions parallel to the plane of the plates 71, 72, 81, 82, 91, 92. The plates 71, 72, 81, 82, 91, 92 have a profile and/or a thickness of between 0.25 mm and 1.5 mm. This profile is sufficient to enable bone material to develop and/or to grow into the pores 77, 87, 97 and between the plates 71, 72, 81, 82, 91, 92. The cage with its open pores 77, 87, 97 can thus be described as osteoconductive. The cage formed from the plates is therefore well suited for connection to the vertebral bodies.

The completed cage comprises two open axial hollow chambers (not shown), which are created by positioning the plates 71, 72, 81, 82, 91, 92 one on top of the other, in which suitably fitting recesses are provided, which are however not shown in FIGS. 17 to 22. The axial hollow chambers and the recesses are structured in the same way as for the preceding exemplary embodiments. The open axial hollow chambers and thus the recesses serve to ensure that bones from the vertebral bodies can grow through them. For this purpose, the surfaces of the open axial hollow chambers and of the recesses are filled with autologous bone replacement material and, if desired, are additionally coated with a substance which promotes bone growth. The free profile of the recesses and of the open axial chambers totals approximately 12 mm, but at least 5 mm, so that the bone of the vertebral bodies can grow in well. The open axial hollow chambers thus form the interior of the cage.

In order to ensure that the open axial hollow chambers are uniform and that the outer form of the cage is even, the plates 71, 72, 81, 82, 91, 92 must be snapped in onto each other flush and/or so that they fit. In order to facilitate this, in the same way as for the first exemplary embodiment, four positioning pins (not shown) respectively can be provided as positioning aids. The plates 71, 72, 81, 82, 91, 92 all have the same shape in relation to the plane of the planar structure 73, 83, 93, so that they can be are placed onto each other in such a manner that they fit.

The kits from all exemplary embodiments can also comprise more plates than those shown, and also groups of plates with different geometries, in order to design the kits as variably as possibly and in order to make them suitable for use in the treatment of different anatomical conditions.

The features of the invention disclosed in the preceding description and in the claims, figures, and exemplary embodiments, can be essential for the implementation of the various embodiments of the invention both alone and in its different combinations.

LIST OF REFERENCE NUMERALS 1, 11, 21, 71, 81, 91 Outer plate
2, 12, 22, 72, 82, 92 Middle plate/inner plate
3, 13, 53, 63, 73, 83, 93 Planar structure
4, 14, 54, 64, 74, 84, 94 Pin
5, 15, 65, 75, 85, 95 Mushroom/latching element
6, 16, 66, 76, 86, 96 Groove/counter snap-in element
7, 67, 77, 87, 97 Pores
8, 18 Open axial hollow chamber
9, 19 Recess
10 Positioning pin
17 Dorsal vertebral body
27 Edge
55, 68 Hook/latching element
69, 79, 89, 99 Engagement surface
A Partial area from FIG. 10 shown enlarged in FIG. 11

The invention claimed is:

1. A modular kit for building a cage for spondylodesis, the kit comprising at least two plates, wherein each plate of the at least two plates consists of a biocompatible material and comprises a planar structure and a plurality of pins projecting from the planar structure, wherein the at least two plates are formed in a shape of a ring, an elliptical ring, or two rings that lie in contact with each other, wherein the planar structure of each plate of the at least two plates is formed by a plate-like base body having a height defined between a first side and an opposing second side of the plate-like base body and an outer edge defining the shape of the at least two plates, wherein each pin of the plurality of pins comprises at least one latching element and is elastically deformable and bendable between the planar structure and at least one latching element, wherein the plurality of pins is arranged sufficiently close to each other on the planar structure such that pressing the planar structures of the at least two plates onto each other causes the latching elements of different plates of the at least two plates to snap into each other to build the cage, wherein each plate of the at least two plates comprises recesses extending through the height of the plate-like base body from the first side to the opposing second side of the plate-like base body and having perimeters surrounded by inner edges of the plate-like base body such that, when the at least two plates snap into each other to build the cage, the cage comprises two open axial hollow chambers formed by the recesses of each plate.

2. The kit according to claim 1, wherein each of the two open axial hollow chambers has a diameter of at least 5 mm.

3. The kit according to claim 2, wherein a wall defining the two open axial hollow chambers is filled with autologous bone material, boundaries of the recesses of the at least two plates are filled with autologous bone material, or the two open axial hollow chambers are filled with autologous bone material.

4. The kit according to claim 1, wherein each recess of the at least two plates has a diameter of at least 5 mm.

5. The kit according to claim 1, wherein the at least two plates snapped into each other form a porous cage.

6. The kit according to claim 1, wherein the kit has an adjustable height and for this purpose comprises at least three plates such that different heights are settable through the optional use of an inner plate or of several inner plates.

7. The kit according to claim 1, wherein the at least two plates comprise circumferential edges, such that the at least two plates snapped into each other form the cage with a closed wall, wherein the circumferential edges of the at least two plates are interlocked.

8. The kit according to claim 1, wherein the at least two plates, in terms of shape of the planar structures, have the same shape or essentially the same shape, such that they are snapped into each other in a form-fit manner in a direction vertical to the planar structures.

9. The kit according to claim 8, wherein the at least two plates, in terms of the shape of the planar structures, have the same shape or essentially the same shape, such that they are snapped into each other in a form-fit manner in the direction vertical to the planar structures, wherein the at least two plates have different geometries with respect to planes defined by the planar structures.

10. The kit according to claim 1, wherein at least two outer plates of the at least two plates, which are provided for direct connection to the vertebral bodies, are osteoconductive due to pores in the planar structures and/or the planar structures comprise an attachment surface without pins, which is designed to be placed against the vertebral bodies, wherein the attachment surface comprises peaks or naps for connecting the plates to the bone of the vertebral bodies.

11. The kit according to claim 1, wherein the planar structures of the at least two plates have a gradient in thickness, wherein an area with the highest thickness is maximum 100% thicker than the area with the lowest thickness.

12. The kit according to claim 1, wherein, on one planar structure of the at least two plates, at least two positioning aids are provided, wherein the at least two positioning aids pre-specify an orientation of the at least two plates to be joined together in relation to one another.

13. The kit according to claim 1, wherein the latching elements are mushrooms, hooks, undercuts, snap-in elements and/or counter snap-in elements.

14. The kit according to claim 1, wherein at least one of the at least one latching elements per pin has a truncated cone shape.

15. The kit according to claim 1, wherein at least one of the at least one latching elements per pin is provided in the form of a hook and/or mushroom head.

16. The kit according to claim 1, wherein the pins between the planar structures of the at least two plates and at least one of the at least one latching elements contain a circumferential groove as a counter-latching means, into which latching elements of other plates of the at least two plates can snap.

17. The kit according to claim 1, wherein the at least two plates are fabricated from biocompatible plastic, stainless steel, titanium, a titanium alloy, tantalum, a tantalum alloy or from composites of these materials.

18. The kit according to claim 1, wherein adjacent pins which are arranged on the same side of a first plate of the at least two plates have such a distance between each other that, following an elastic deformation due to a snapped-in connection with a latching element of a second plate of the at least two plates, the pins of the first plate enable at least two snapped-in connections with at least two further latching elements of the second plate.

19. The kit according to claim 1, wherein the at least two plates are filled with inorganic or organic particular bone replacement material and/or autologous or also allogenic cancellous bone.

20. The kit according to claim 1, wherein the at least two plates are coated with one or more pharmaceutical agents from the groups of antibiotics, bisphosphonates, steroids, non-steroidal anti-inflammatory drugs, growth factors and cytostatic agents.

21. The kit according to claim 1, wherein the pins are arranged in rows of three or more pins, respectively, and that between these three or more rows respectively a strip of unoccupied surface of the planar structures remains.

22. The kit according to claim 1, wherein the kit comprises at least two outer plates for connection to the vertebral bodies and at least one inner plate for setting the height of the cage to be built, wherein each of the at least one inner plate comprises pins with latching elements on both sides of the planar structure, and the at least two outer plates comprise pins with latching elements on only one side of the planar structures.

23. A method for building a cage for spondylodesis with the kit according to claim 1, the method comprising:
pressing several plates of the at least two plates against each other such that the several plates snap into each other and form the cage.

24. The method according to claim 23, wherein, depending on the desired thickness of the cage to be built, none, one or several inner plates of the at least two plates is/are inserted between two outer plates of the at least two plates, wherein the plates of the at least two plates are snapped into each other by being pressed on top of each other and as a result are firmly connected to each other.

25. A cage for spondylodesis constructed of the at least two plates from the kit according to claim 1.

* * * * *